US011051992B2

(12) United States Patent
Kawka et al.

(10) Patent No.: US 11,051,992 B2
(45) **Date of Patent: *Jul. 6, 2021**

(54) SYSTEMS AND METHODS FOR INSPECTING ABSORBENT ARTICLES ON A CONVERTING LINE

(71) Applicant: The Procter & Gamble Company, Cincinnati, OH (US)

(72) Inventors: Paul Anthony Kawka, Cleves, OH (US); Stephen Michael Varga, Loveland, OH (US); Aitzaz Ahmad, Mason, OH (US); Paul Philip Thomas, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/827,840

(22) Filed: Mar. 24, 2020

(65) Prior Publication Data

US 2020/0222247 A1 Jul. 16, 2020

Related U.S. Application Data

(63) Continuation of application No. 15/993,698, filed on May 31, 2018, now Pat. No. 10,632,023.

(Continued)

(51) Int. Cl.

*A61F 13/15* (2006.01)
*G06N 3/04* (2006.01)

(Continued)

(52) U.S. Cl.

CPC .. *A61F 13/15585* (2013.01); *A61F 13/15772* (2013.01); *A61F 13/49* (2013.01);

(Continued)

(58) Field of Classification Search

CPC .............. A61F 13/495; A61F 13/15772; A61F 13/15585; A61F 13/49009;

(Continued)

(56) References Cited

U.S. PATENT DOCUMENTS 2,075,189 A 3/1937 Galligan et al.
3,025,199 A 3/1962 Harwood (Continued)

FOREIGN PATENT DOCUMENTS

EP 1528907 B1 9/2008

OTHER PUBLICATIONS

P&G 14852C, All Office Actions for U.S. Appl. No. 16/827,823.
All Office Actions; U.S. Appl. No. 15/993,677.
All Office Actions; U.S. Appl. No. 15/993,698.

*Primary Examiner* — Daniel G Mariam
(74) *Attorney, Agent, or Firm* — Jay A. Krebs

(57) ABSTRACT

A method for inspecting absorbent articles is provided. The inspection is performed using an inspection algorithm generated with a convolutional neural network having convolutional neural network parameters. The convolutional neural network parameters are generated by a training algorithm. Based on the inspection, characteristics of the absorbent articles, such as defects, can be identified. Absorbent articles having identified characteristics can be rejected, or other actions can be taken.

20 Claims, 10 Drawing Sheets

122 146 150 140,142 164 162 118 152 154 106 104 130 128 124 119 PL 100,100T 126 132,138 156 156 102 134,136 116 168b 148 110 108 120 168a 168 144

Related U.S. Application Data

(60) Provisional application No. 62/518,711, filed on Jun. 13, 2017.

(51) Int. Cl.

| | |
|---|---|
| ***G06T 7/00*** | (2017.01) |
| ***G06N 3/08*** | (2006.01) |
| ***G06T 7/187*** | (2017.01) |
| ***G06T 7/11*** | (2017.01) |
| ***A61F 13/49*** | (2006.01) |
| ***G06N 5/04*** | (2006.01) |
| *B32B 5/26* | (2006.01) |
| *D04H 1/593* | (2012.01) |
| *A61F 13/495* | (2006.01) |
| *B32B 5/32* | (2006.01) |

(52) U.S. Cl.

CPC ............ *G06N 3/0454* (2013.01); *G06N 3/08* (2013.01); *G06N 5/046* (2013.01); *G06T 7/0002* (2013.01); *G06T 7/0004* (2013.01); *G06T 7/11* (2017.01); *G06T 7/187* (2017.01); *G06T 7/97* (2017.01); *A61F 13/495* (2013.01); *A61F 13/49009* (2013.01); *A61F 2013/1578* (2013.01); *A61F 2013/15788* (2013.01); *A61F 2013/15796* (2013.01); *B32B 5/26* (2013.01); *B32B 5/32* (2013.01); *D04H 1/593* (2013.01); *G06T 2207/30108* (2013.01)

(58) Field of Classification Search

CPC .... A61F 2013/1578; A61F 2013/15788; A61F 2013/15796; B32B 5/26; B32B 5/32; G06N 3/0454; G06N 5/046; G06T 7/0002; G06T 7/0004; G06T 7/11; G06T 7/97; G06T 7/187; G06T 2207/30108; D04H 1/593

USPC ........................................ 382/144, 149, 204

See application file for complete search history.

(56) References Cited

U.S. PATENT DOCUMENTS 3,848,594 A 11/1974 Buell
3,860,003 A 1/1975 Buell
4,107,364 A 8/1978 Sisson
4,209,563 A 6/1980 Sisson
4,515,595 A 5/1985 Kievit et al.
4,610,678 A 9/1986 Weisman et al.
4,662,875 A 5/1987 Hirotsu et al.
4,673,402 A 6/1987 Weisman et al.
4,695,278 A 9/1987 Lawson
4,704,115 A 11/1987 Buell
4,795,454 A 1/1989 Dragoo
4,834,735 A 5/1989 Alemany et al.
4,834,741 A 5/1989 Sabee
4,846,815 A 7/1989 Scripps
4,854,984 A 8/1989 Ball et al.
4,888,231 A 12/1989 Angstadt
4,894,060 A 1/1990 Nestegard
4,909,803 A 3/1990 Aziz et al.
4,940,464 A 7/1990 Van Gompel et al.
4,946,527 A 8/1990 Battrell
5,092,861 A 3/1992 Nomura et al.
5,151,092 A 9/1992 Buell et al.
5,167,897 A 12/1992 Weber et al.
5,221,274 A 6/1993 Buell et al.
5,246,433 A 9/1993 Hasse et al.
5,286,543 A 2/1994 Ungpiyakul et al.
5,330,458 A 7/1994 Buell et al.
5,359,525 A 10/1994 Weyenberh
5,360,420 A 11/1994 Cook et al.
5,562,646 A 10/1996 Goldman et al.
5,569,234 A 10/1996 Buell et al.
5,599,335 A 2/1997 Goldman et al.
5,628,097 A 5/1997 Benson et al.
5,643,588 A 7/1997 Roe et al.
5,669,894 A 9/1997 Goldman et al.
5,674,216 A 10/1997 Buell et al.
5,702,551 A 12/1997 Huber et al.
5,735,840 A 4/1998 Kline et al.
5,897,545 A 4/1999 Kline et al.
5,916,661 A 6/1999 Benson et al.
5,928,212 A 7/1999 Kline et al.
5,957,908 A 9/1999 Kline et al.
5,968,025 A 10/1999 Roe et al.
6,107,537 A 8/2000 Elder et al.
6,107,539 A 8/2000 Palumbo et al.
6,118,041 A 9/2000 Roe et al.
6,120,487 A 9/2000 Ashton
6,120,489 A 9/2000 Johnson et al.
6,153,209 A 11/2000 Vega et al.
6,248,195 B1 6/2001 Schmitz
6,251,097 B1 6/2001 Kline et al.
6,410,129 B2 6/2002 Zhang et al.
6,426,444 B2 7/2002 Roe et al.
6,432,098 B1 8/2002 Kline et al.
6,450,321 B1 9/2002 Blumenthal et al.
6,545,197 B1 4/2003 Muller et al.
6,586,652 B1 7/2003 Roe et al.
6,617,016 B2 9/2003 Zhang et al.
6,627,787 B1 9/2003 Roe et al.
6,669,618 B2 12/2003 Reising et al.
6,705,453 B2 3/2004 Blumenthal et al.
6,790,798 B1 9/2004 Suzuki et al.
6,801,828 B2 10/2004 Popp et al.
6,811,019 B2 11/2004 Christian et al.
6,814,217 B2 11/2004 Blumenthal et al.
6,820,022 B2 11/2004 Popp et al.
6,825,393 B2 11/2004 Roe et al.
6,861,571 B1 3/2005 Roe et al.
7,123,981 B2 10/2006 Dollevoet et al.
7,371,302 B2 5/2008 Miyamoto et al.
8,145,338 B2 3/2012 Kent et al.
8,145,343 B2 3/2012 DeBruler et al.
8,145,344 B2 3/2012 DeBruler et al.
2003/0233082 A1 12/2003 Kline et al.
2004/0097895 A1 5/2004 Busam et al.
2004/0158212 A1 8/2004 Ponomarenko et al.
2007/0078427 A1 4/2007 Raycheck et al.
2007/0093769 A1 4/2007 Kline et al.
2008/0110984 A1* 5/2008 Uchitani .............. A61F 15/001 235/385
2009/0312730 A1 12/2009 LaVon et al.
2013/0072887 A1 3/2013 LaVon et al.
2013/0211356 A1 8/2013 Nishikawa et al.
2013/0306226 A1 11/2013 Zink et al.
2017/0227462 A1 8/2017 Varga
2018/0353348 A1 12/2018 Kawka
2018/0357756 A1 12/2018 Kawka
2020/0222247 A1 7/2020 Kawka

* cited by examiner

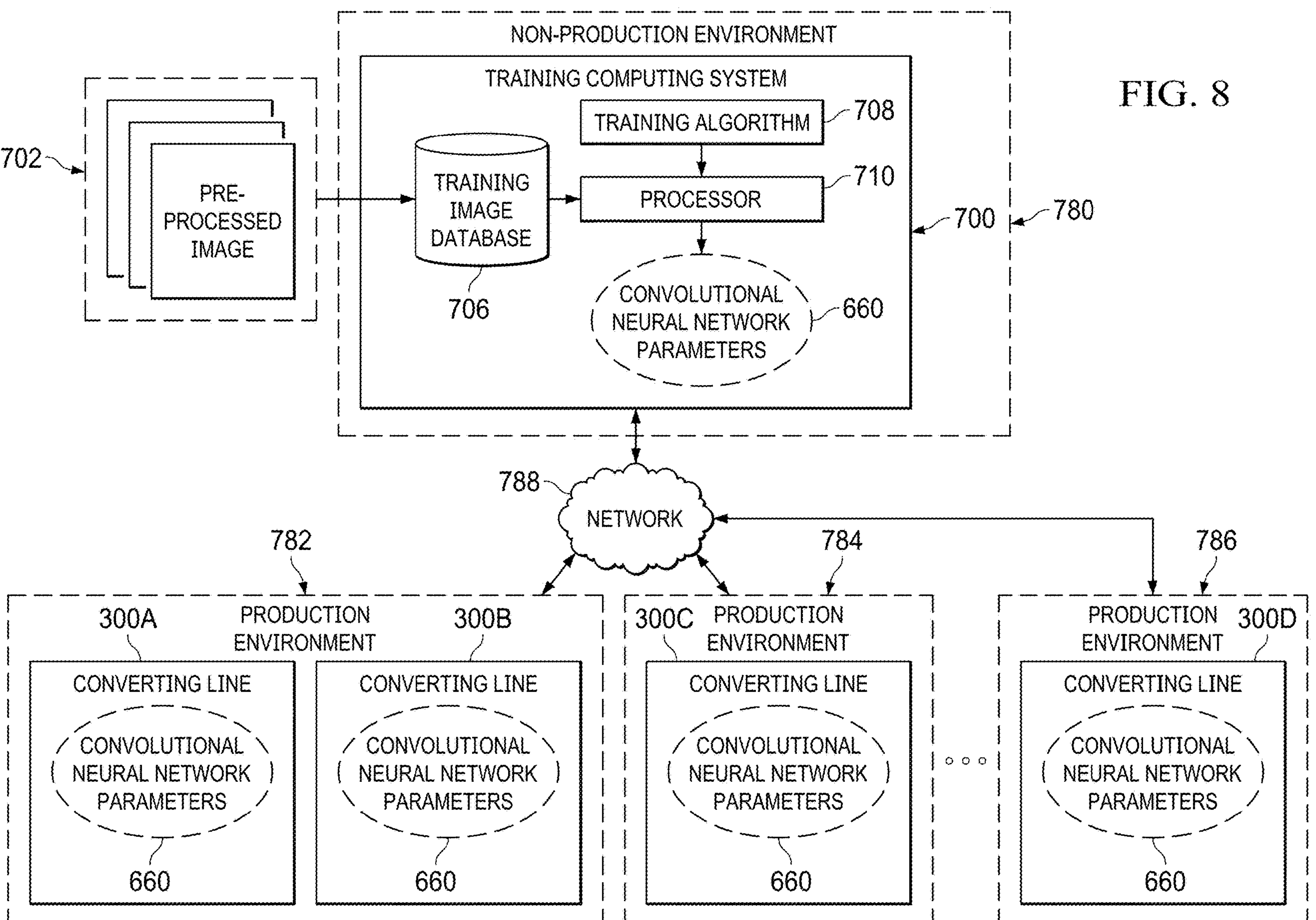
FIG. 8
NON-PRODUCTION ENVIRONMENT
TRAINING COMPUTING SYSTEM
TRAINING ALGORITHM
708
702
PRE-PROCESSED IMAGE
TRAINING IMAGE DATABASE
PROCESSOR
710
700
780
706
CONVOLUTIONAL NEURAL NETWORK PARAMETERS
660
788
NETWORK
782
784
786
300A
PRODUCTION ENVIRONMENT
300B
300C
PRODUCTION ENVIRONMENT
PRODUCTION ENVIRONMENT
300D
CONVERTING LINE
CONVOLUTIONAL NEURAL NETWORK PARAMETERS
660
CONVERTING LINE
CONVOLUTIONAL NEURAL NETWORK PARAMETERS
660
CONVERTING LINE
CONVOLUTIONAL NEURAL NETWORK PARAMETERS
660
CONVERTING LINE
CONVOLUTIONAL NEURAL NETWORK PARAMETERS
660

SYSTEMS AND METHODS FOR INSPECTING ABSORBENT ARTICLES ON A CONVERTING LINE

CROSS REFERENCE TO RELATED APPLICATIONS

This application is a continuation of U.S. application Ser. No. 15/993,698, filed on May 31, 2018, which claims the benefit of U.S. Provisional Application No. 62/518,711, filed Jun. 13, 2017, both of which are herein incorporated by reference.

FIELD OF THE INVENTION

The present disclosure relates to systems and methods for manufacturing disposable absorbent articles, and more particularly, systems and methods for inspecting substrates and components on a converting apparatus utilizing an inspection algorithm generated with a convolutional neural network.

BACKGROUND OF THE INVENTION

Along an assembly line, diapers and various types of other absorbent articles may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

For quality control purposes, absorbent article converting lines may utilize various types of sensor technology to inspect the webs and discrete components added to the webs along the converting line as absorbent articles are constructed. Example sensor technology may include vision systems, photoelectric sensors, proximity sensors, laser or sonic distance detectors, and the like. Product inspection data from the sensors may be communicated to a controller in various ways. In turn, the controller may be programmed to receive product inspection data, and in turn, make adjustments to the manufacturing process. In some instances, the controller may reject defective absorbent articles based on the product inspection data after the final knife cut at the end of the converting line.

As such, the controller may be programmed with various algorithms adapted to analyze the inspection data and provide desired control functions to the manufacturing process. The complexity and sophistication of the algorithms may vary with the type of inspection data being analyzed. In some configurations, a vision system may be configured to communicate image data from an inspection zone to a controller, wherein aspects of the image data may be analyzed by an algorithm to determine whether control actions should be executed. For example, the image data may be analyzed to determine whether a component is missing or improperly positioned during the assembly process. Depending upon whether other features, such as graphics, bond patterns, or wrinkles, also may be located in the inspection zone, the algorithm may need to be relatively more complex to enable the algorithm to distinguish the component or lack thereof from such other features in the inspection zone.

However, limitations of human generated inspection algorithms currently constrain the speed of algorithm development and the scope of what can be inspected. Consequently, it would be beneficial to generate and utilize algorithms capable of inspections that otherwise cannot be coded by humans to conduct relatively more sophisticated in-process inspection operations of assembled absorbent articles.

SUMMARY OF THE INVENTION

In one form, a method comprises preprocessing each image of a group of images of absorbent articles to label a component of the absorbent article. The method further comprises generating a first inspection algorithm with a convolutional neural network based on the preprocessed images. The first inspection algorithm is usable to mask the labeled component in images of absorbent articles. The method further comprises providing a second inspection algorithm. The second inspection algorithm is usable to determine one or more properties of the labeled component in images of absorbent articles. The one or more properties comprise any of a location, a size, a shape, and a presence of the component. The method further comprises providing a communication network, connecting a sensor with the communication network and connecting a controller with the communication network. The controller comprises the first inspection algorithm. The method further comprises advancing a substrate through a converting process, sequentially adding component parts to the substrate, and creating images of at least one of the substrate and component parts with the sensor. The method further comprises communicating the images from the sensor to the controller and masking the labeled component in the images by analyzing the images with the first inspection algorithm. The method further comprises determining at least one of the properties for the labeled component in the substrate with the second inspection algorithm. The method further comprises cutting the substrate with component parts added thereto into discrete absorbent articles. The method further comprises based on the determination of the least one of the properties for the labeled component in the substrate, executing a control action. The control action is any of rejecting one or more of the discrete absorbent articles, an automatic phase adjustment, an automatic tracking adjustment, a machine maintenance scheduling, and a machine stop command.

In another form, a method comprises preprocessing each image of a group of images of absorbent articles to label a component of the absorbent article. The method further comprises generating a first inspection algorithm with a convolutional neural network based on the preprocessed images. The first inspection algorithm is usable to mask the labeled component in images of absorbent articles. The method further comprises providing a second inspection algorithm. The second inspection algorithm is usable to determine one or more properties of the labeled component in images of absorbent articles. The one or more properties comprise any of a location, a size, a shape, and a presence of the component. The method further comprises advancing a substrate through a converting process and sequentially adding component parts to the substrate. The method further comprises creating images of a substrate and one or more component parts. The method further comprises masking the labeled component in the images by analyzing the images with the first inspection algorithm. The method further comprises determining at least one of the properties for the labeled component in the substrate with the second inspection algorithm.

In yet another form, a method comprises storing a group of digitized signals of absorbent articles. The digitized signals are preprocessed to label a component of the absorbent article. The method further comprises providing the preprocessed digitized signals to a training algorithm to create a convolutional neural network and generating a first inspection algorithm with the convolutional neural network based on the group of preprocessed digitized signals. The first inspection algorithm masks one or more properties of the labeled component. The method further comprises providing a second inspection algorithm. The second inspection algorithm is usable to determine one or more properties of the labeled component in digitized signals of absorbent articles. The one or more properties comprise any of a location, a size, a shape, and a presence of the component. The method further comprises advancing a substrate through a converting process, and sequentially adding component parts to the substrate. The method further comprises creating inspection data of at least one of the substrate and component parts with a sensor and communicating the inspection data from the sensor to a controller. The controller comprises the first inspection algorithm. The method further comprises identifying the labeled component in the substrate by analyzing the inspection data with the first inspection algorithm. The method further comprises determining at least one of the properties for the labeled component in the substrate with the second inspection algorithm. The method further comprises cutting the substrate with component parts added thereto into discrete absorbent articles.

BRIEF DESCRIPTION OF THE DRAWINGS

FIG. 8 is a block diagram of a centralized training computing system positioned remote from a plurality of production environments.

DETAILED DESCRIPTION OF THE INVENTION

Figure 1A:
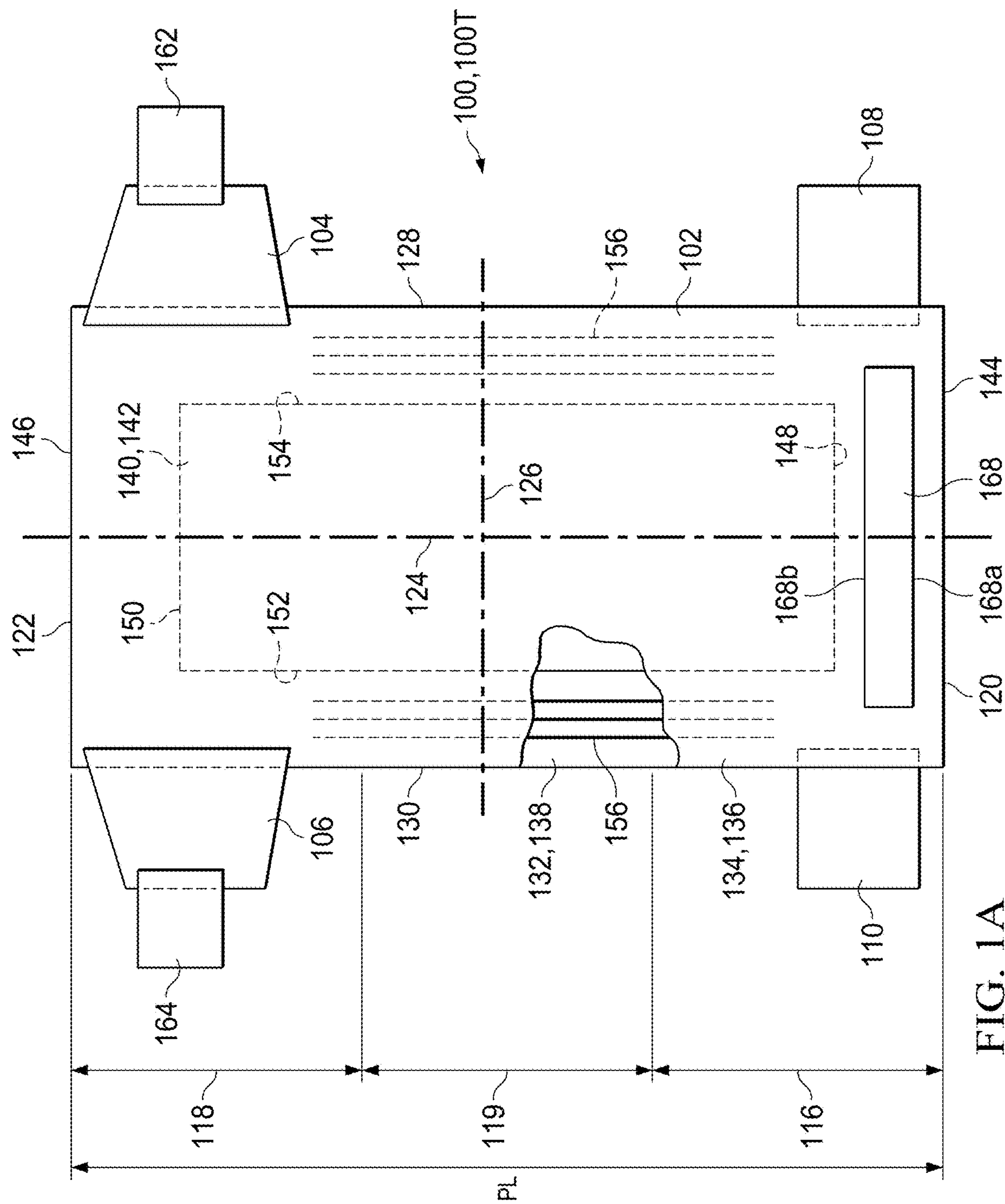
FIG. 1A is a partially cut away plan view of an absorbent article in the form of a taped diaper that may include one or more substrates and/or components inspected and/or controlled in accordance with the present disclosure with the portion of the diaper that faces away from a wearer oriented towards the viewer.

The following term explanations may be useful in understanding the present disclosure: "Absorbent article" is used herein to refer to consumer products whose primary function is to absorb and retain soils and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 5,246,433; 5,569,234; 6,120,487; 6,120,489; 4,940, 464; 5,092,861; 5,897,545; 5,957,908; and U.S. Patent Publication No. 2003/0233082 A1.

An “elastic,” “elastomer” or “elastomeric” refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term “joined” encompasses configurations whereby an element is directly secured to another element by affixing the element directly to the other element, and configurations whereby an element is indirectly secured to another element by affixing the element to intermediate member(s) which in turn are affixed to the other element.

The term “substrate” is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term “machine direction” (MD) is used herein to refer to the direction of material flow through a process. In addition, relative placement and movement of material can be described as flowing in the machine direction through a process from upstream in the process to downstream in the process.

The term “cross direction” (CD) is used herein to refer to a direction that is generally perpendicular to the machine direction.

The present disclosure relates to systems and processes manufacturing absorbent articles. More particularly, the systems and processes herein may be configured to inspect substrates and components on a converting apparatus utilizing an inspection algorithm generated with a convolutional neural network. During the manufacture of absorbent articles, a substrate may be advanced through a converting process while combining with other substrates and/or adding component parts to the substrate. In turn, the substrate with component parts added thereto may be cut into discrete absorbent articles. As such, an inspection system may be configured to inspect the substrate and/or component parts during the assembly process. As discussed in more detail below, the inspection system may include a controller and a sensor. The controller includes an inspection algorithm generated with a convolutional neural network based on convolutional neural network parameters. The inspection algorithm may be created based in part from a group of images of absorbent articles. Each of the images may be preprocessed to label a component of the absorbent article. The component may be, for instance, a landing zone, an ear, a tab, among a variety of other features or attributes, including contaminants such as a foreign material, grease, or dirt, or other undesirable transformation of the absorbent article such a tear, a wrinkle, a fold, and so forth. In addition to labeling a component, preprocessing the image can optionally include cropping the image, scaling the image, resizing the image, and so forth. The preprocessed images may then be provided to a training algorithm to create the convolutional neural network parameters used to generate the inspection algorithm. During inspection operations, the sensor may be adapted to create inspection data of at least one of the substrate and component parts, and then communicate the inspection data to the controller. The labeled components of the substrate and component parts from the training set may then be identified by analyzing the inspection data with the inspection algorithm. Subsequent to identifying the labeled component, a second inspection algorithm may then be utilized to identify one or more properties of the labeled component. In turn, the controller may execute a control action based on properties of the identified component.

Figure 1B:
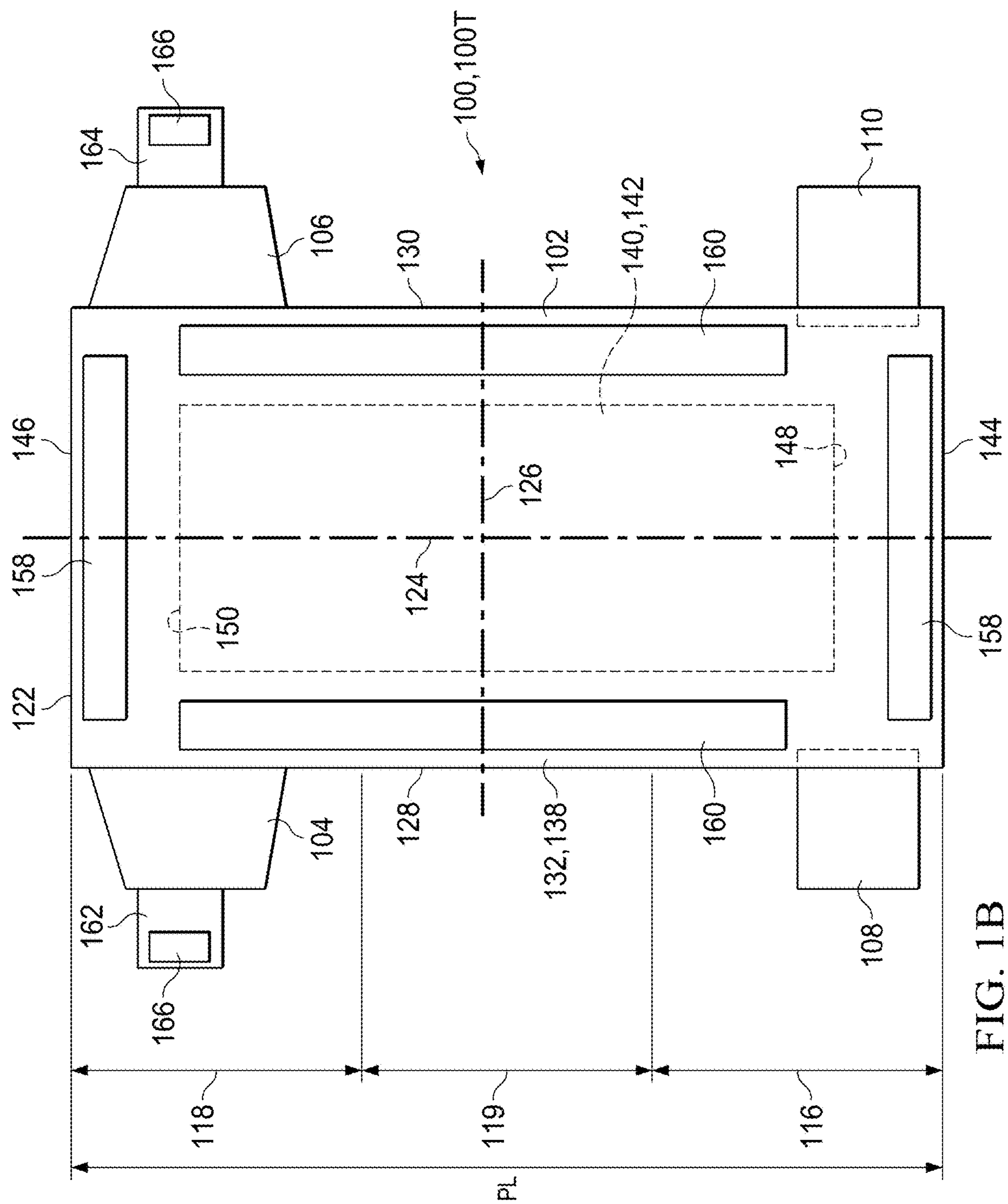
FIG. 1B is a plan view of the absorbent article of FIG. 1A that may include one or more substrates and/or components monitored and/or controlled in accordance with the present disclosure with the portion of the diaper that faces toward a wearer oriented towards the viewer.

It is to be appreciated that the systems and methods disclosed herein are applicable to work with various types of converting processes and/or machines, such as for example, absorbent article manufacturing, and/or packaging processes. For illustration purposes, the methods and apparatuses are discussed below in the context of manufacturing diapers, although this disclosure is not so limited. The methods and apparatuses are applicable to converting processes for feminine hygiene products, for example. For the purposes of a specific illustration, FIGS. 1A and 1B show an example of an absorbent article 100 that may be assembled in accordance with the methods and apparatuses disclosed herein. In particular, FIG. 1A shows one example of a plan view of an absorbent article 100 configured as a taped diaper 100T, with the portion of the diaper that faces away from a wearer oriented towards the viewer. And FIG. 1B shows a plan view of the diaper 100 with the portion of the diaper that faces toward a wearer oriented towards the viewer. The taped diaper 100T shown in FIGS. 1A and 1B includes a chassis 102, first and second rear side panels 104 and 106; and first and second front side panels 108 and 110.

As shown in FIGS. 1A and 1B, the diaper 100 and the chassis 102 each include a first waist region 116, a second waist region 118, and a crotch region 119 disposed intermediate the first and second waist regions. The first waist region 116 may be configured as a front waist region, and the second waist region 118 may be configured as back waist region. In some configurations, the length of each of the front waist region, back waist region, and crotch region may be 1/3 of the length of the absorbent article 100. The absorbent article may also include a laterally extending front waist edge 120 in the front waist region 116 and a longitudinally opposing and laterally extending back waist edge 122 in the back waist region 118. To provide a frame of reference for the present discussion, the diaper 100T in FIGS. 1A and 1B is shown with a longitudinal axis 124 and a lateral axis 126. The longitudinal axis 124 may extend through a midpoint of the front waist edge 120 and through a midpoint of the back waist edge 122. And the lateral axis 126 may extend through a midpoint of a first longitudinal or right side edge 128 and through a midpoint of a second longitudinal or left side edge 130.

As shown in FIGS. 1A and 1B, the diaper 100 includes an inner, body facing surface 132, and an outer, garment facing surface 134. And the chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs, an elastic waist region, and/or flaps, e.g., side panels and/or ears, to enhance the fits around the legs and waist of the wearer, to enhance the fit around the legs of the wearer.

As shown in FIGS. 1A and 1B, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 1A, the laterally extending end edges 144 and 146 may form a portion of the laterally extending front waist edge 120 in the front waist region 116 and a portion of the longitudinally opposing and laterally extending back waist edge 122 in the back waist region 118. The distance between the first lateral end edge 144 and the second lateral end edge 146 may define a pitch length, PL, of the chassis 102. When the diaper 100 is worn on the lower torso of a wearer, the front waist edge 120 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, the user of the diaper 100, including a chassis 102 having a particular size before extension, to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

The diaper 100 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper 100 may also include an absorbent assembly 140 that is joined to the chassis 102. As shown in FIGS. 1A and 1B, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core configurations may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/0097895 A1.

The diaper 100 may also include elasticized leg cuffs 156 and an elasticized waistband 158. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; and U.S. Patent Publication No. 2009/0312730 A1.

The elasticized waistband 158 may provide improved fit and containment and may be a portion or zone of the diaper 100 that may elastically expand and contract to dynamically fit a wearer's waist. The elasticized waistband 158 may extend longitudinally inwardly from the waist edges 120, 122 of the diaper toward the lateral edges 148, 150 of the absorbent core 142. The diaper 100 may also include more than one elasticized waistband 158, for example, having one waistband 158 positioned in the back waist region 118 and one waistband 158 positioned in the front wait region 116, although other configurations may be constructed with a single elasticized waistband 158. The elasticized waistband 158 may be constructed in a number of different configurations including those described in U.S. Pat. Nos. 4,515,595 and 5,151,092. In some configurations, the elasticized waistbands 158 may include materials that have been "prestrained" or "mechanically prestrained" (subjected to some degree of localized pattern mechanical stretching to permanently elongate the material). The materials may be prestrained using deep embossing techniques as are known in the art. In some configurations, the materials may be prestrained by directing the material through an incremental mechanical stretching system as described in U.S. Pat. No. 5,330,458. The materials are then allowed to return to their substantially untensioned condition, thus forming a zero strain stretch material that is extensible, at least up to the point of initial stretching. Examples of zero strain materials are disclosed in U.S. Pat. Nos. 2,075,189; 3,025,199; 4,107,364; 4,209,563; 4,834,741; and 5,151,092.

As shown in FIG. 1B, the chassis 102 may include longitudinally extending and laterally opposing side flaps 160 that are disposed on the interior surface 132 of the chassis 102 that faces inwardly toward the wearer and contacts the wearer. Each side flap may have a proximal edge. The side flaps may also overlap the absorbent assembly 140, wherein the proximal edges extend laterally inward of the respective side edges of the absorbent assembly 152 and 154. In some configurations, the side flaps may not overlap the absorbent assembly. It is to be appreciated that the side flaps may be formed in various ways, such as for example, by folding portions of the chassis 102 laterally inward, i.e., toward the longitudinal axis 124, to form both the respective side flaps and the side edges 128 and 130 of the chassis 102. In another example, the side flaps may be formed by attaching an additional layer or layers to the chassis at or adjacent to each of the respective side edges and of the chassis. Each of the side flaps may be joined to the interior surface 132 of the chassis and/or the absorbent assembly in side flap attachment zones in the front waist region 116 and in side flap attachment zones in the back waist region 118. The side flaps may extend to the same longitudinal extent as the absorbent article or alternatively the side flaps may have a longitudinal extent that is less than the absorbent article.

Taped diapers may be manufactured and provided to consumers in a configuration wherein the front waist region and the back waist region are not fastened, pre-fastened, or connected to each other as packaged, prior to being applied to the wearer. For example, the taped diaper 100 may be folded about a lateral centerline with the interior surface 132 of the first waist region 116 in surface to surface contact with the interior surface 132 of the second waist region 118 without fastening or joining the waist regions together. The rear side panels 104 and 106 and/or the front side panels 108 and 110 may also be folded laterally inward toward the inner surfaces 132 of the waist regions 116 and 118.

The diaper 100 may also include various configurations of fastening elements to enable fastening of the front waist region 116 and the back waist region 118 together to form a closed waist circumference and leg openings once the diaper is positioned on a wearer. For example, as shown in FIGS. 1A and 1B, the diaper 100 may include first and second fastening members 162, 164, also referred to as tabs, connected with the first and second rear side panels 104, 106, respectively. The diaper may also include first and second front side panels 108, 110, that may or may not include fastening members.

With continued reference to FIGS. 1A and 1B, each side panel 104, 106 and/or fastening member 162 and 164 may form a portion of or may be permanently bonded, adhered or otherwise joined directly or indirectly to the chassis 102 laterally inward from the side edge 128 and 130, in one of the front waist region 116 or the back waist region 118. Alternatively, the fastening members 162, 164 may form a portion of or may be permanently bonded, adhered or otherwise joined directly or indirectly to the first and second rear panels 104, 106 at or adjacent the distal edge of the panel and/or the first and second front side panels 108 and 110 at or adjacent the distal edge of the side panel. It is to be appreciated that the fastening members and/or side panels may be assembled in various ways, such as disclosed for example, in U.S. Pat. No. 7,371,302. The fastening members 162, 164 and/or side panels 104, 106, 108, 110 may also be permanently bonded or joined at or adjacent the side edges 128 and 130 of the chassis 102 in various ways, such as for example, by adhesive bonds, sonic bonds, pressure bonds, thermal bonds or combinations thereof, such as disclosed for example, U.S. Pat. No. 5,702,551.

Referring now to FIG. 1B, the first fastening member 162 and/or the second fastening member 164 may include various types of releasably engageable fasteners. The first and second fastening members 162 and/or 164 may also include various types of refastenable fastening structures. For example, the first and second fastening members 162 and 164 may include mechanical fasteners, 166, in the form of hook and loop fasteners, hook and hook fasteners, macrofasteners, buttons, snaps, tab and slot fasteners, tape fasteners, adhesive fasteners, cohesive fasteners, magnetic fasteners, hermaphroditic fasteners, and the like. Some examples of fastening systems and/or fastening members 162, 164 are discussed in U.S. Pat. Nos. 3,848,594; 4,662,875; 4,846,815; 4,894,060; 4,946,527; 5,151,092; 5,221,274; 6,251,097; 6,669,618; 6,432,098; and U.S. Patent Publication Nos. 2007/0078427 A1 and 2007/0093769 A1.

The fastening members 162 and 164 may be constructed from various materials and may be constructed as a laminate structure. The fastening members 162 and 164 may also be adapted to releasably and/or refastenably engage or connect with another portion of the diaper 100. For example, as shown in FIG. 1A, the diaper 100 may include a connection zone 168, sometimes referred to as a landing zone, in the first waist region 116. As such, when the taped diaper 100 is placed on a wearer, the fastening members 162 and 164 may be pulled around the waist of the wearer and connected with the connection zone 168 in the first waist region 116 to form a closed waist circumference and a pair of laterally opposing leg openings. It is to be appreciated that the connection zone may be constructed from a separate substrate that is connected with the chassis 102 of the taped diaper, such as shown in FIG. 1A. As such, the connection zone 168 may have a pitch length PL defined by a distance extending between a first lateral end edge 168*a* and the second lateral end edge 168*b*. In some configurations, the connection zone may be integrally formed as part of the backsheet 136 of the diaper 100 or may be formed as part of the first and second front panels 108, 110, such as described in U.S. Pat. Nos. 5,735,840 and 5,928,212.

Figure 2A:
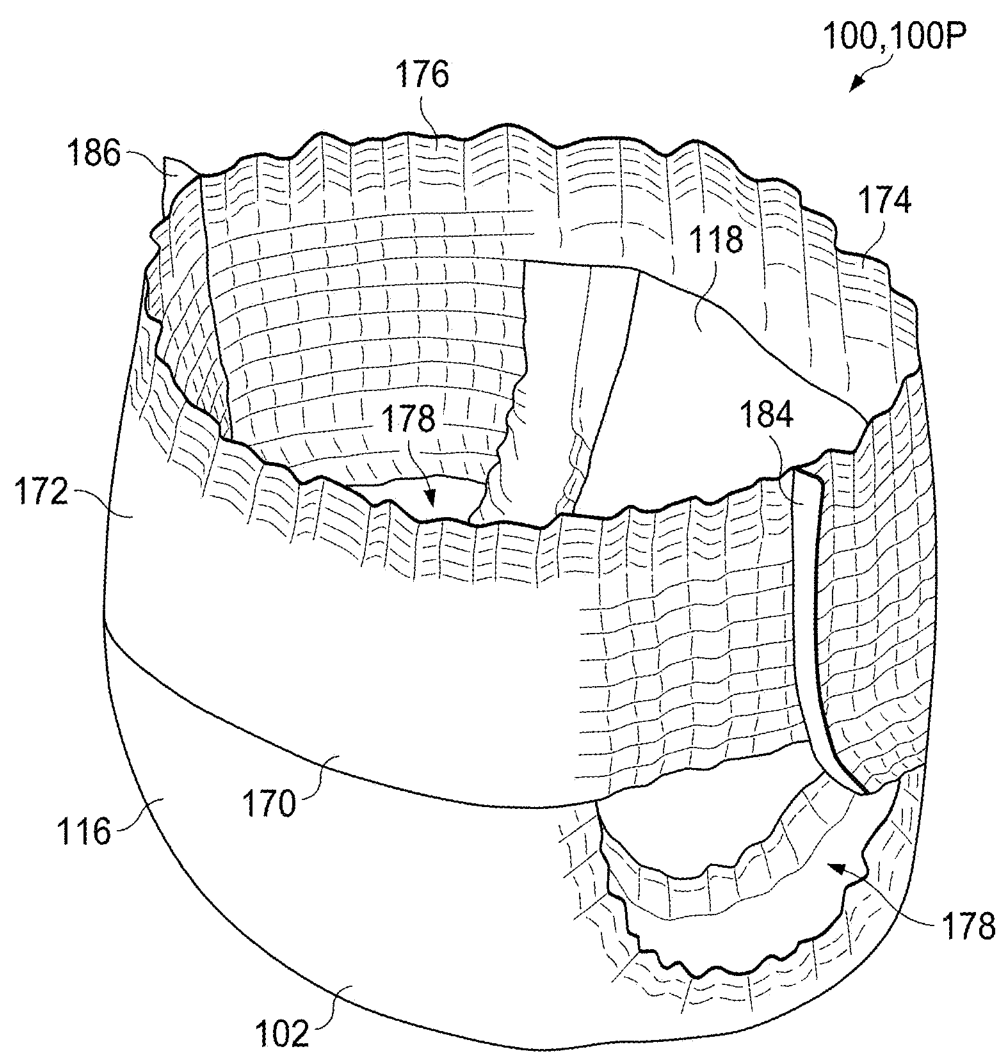
FIG. 2A is a front perspective view of an absorbent article in the form of a diaper pant that may include one or more substrates and/or components inspected and/or controlled in accordance with the present disclosure.
Figure 2B:
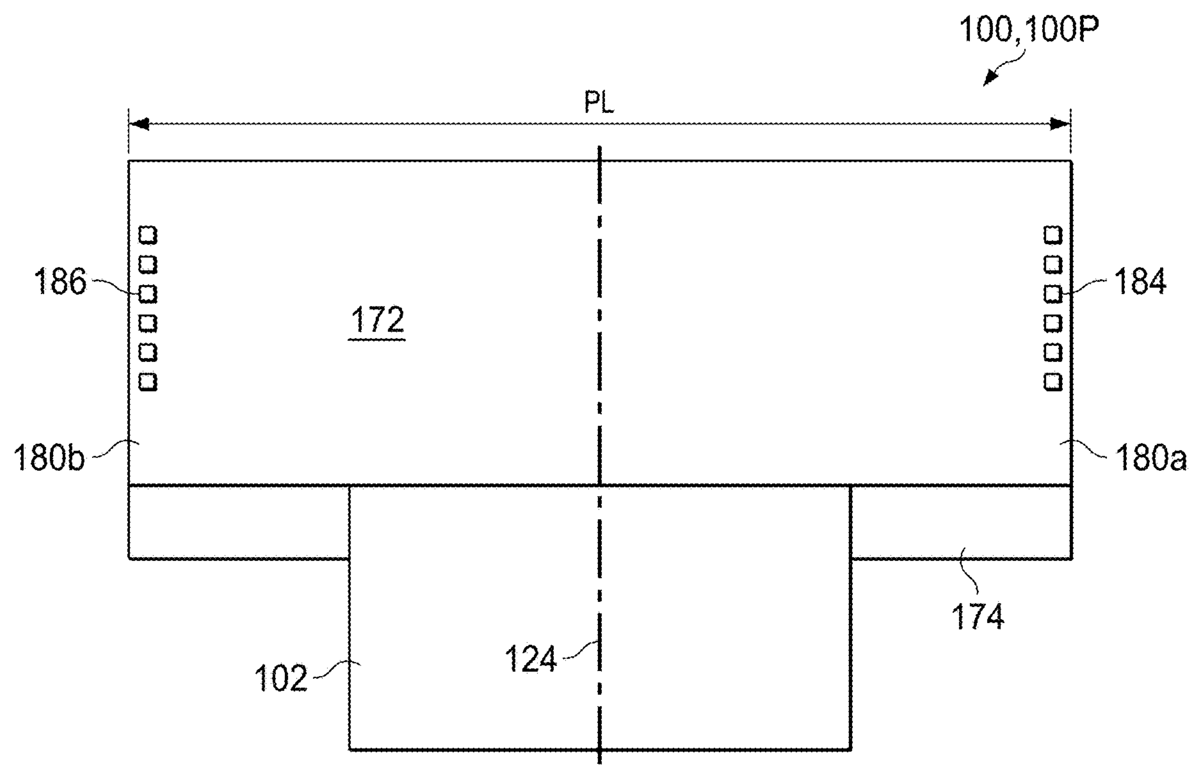
FIG. 2B is a front view of the absorbent article of FIG. 2A.
Figure 2C:
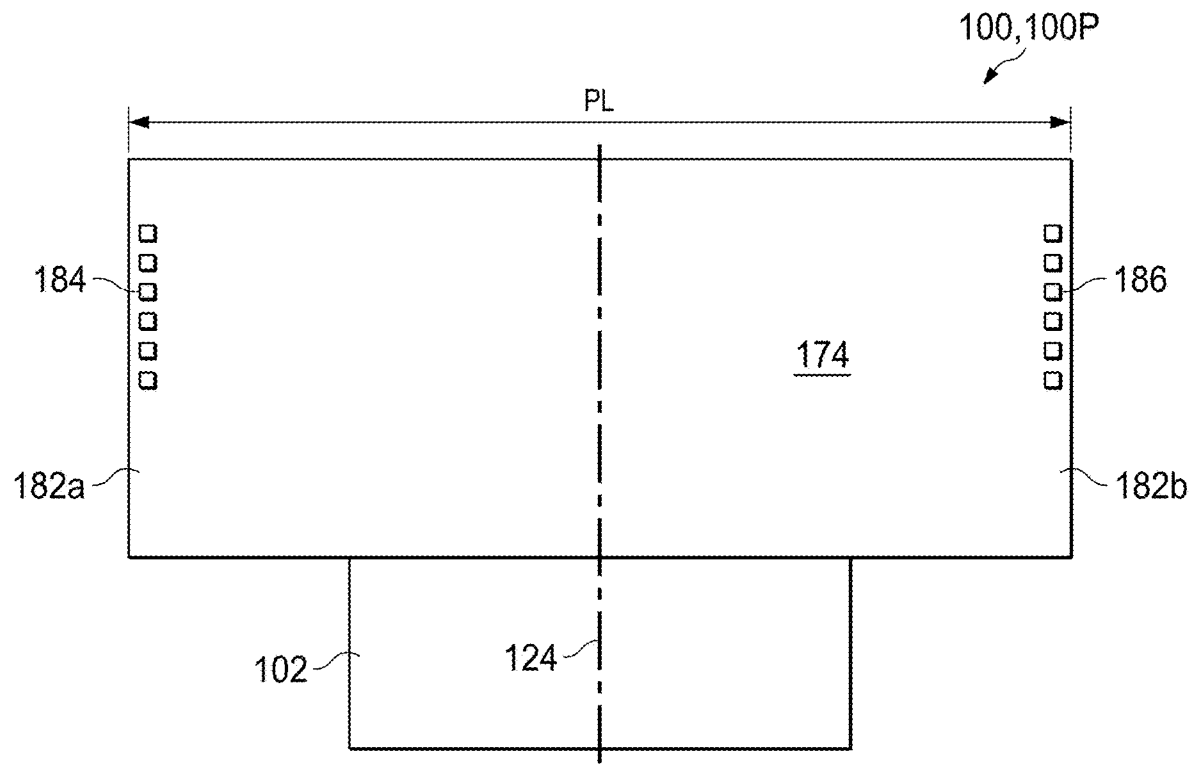
FIG. 2C is a rear view of the absorbent article of FIG. 2A.

Absorbent articles 100 may also be configured as diaper pants 100P having a continuous perimeter waist opening and continuous perimeter leg openings. For example, FIG. 2A shows a perspective view of an absorbent article 100 in the form of a diaper pant 100P in a pre-fastened configuration, and FIGS. 2B-2C show front and rear plan views of the diaper pant 100P. The diaper pant 100P may include a chassis 102 such a discussed above with reference to FIG. 1A and a ring-like elastic belt 170 such as shown in FIG. 2A. In some configurations, a first elastic belt 172 and a second elastic belt 174 are bonded together to form the ring-like elastic belt 170. As such, diaper pants may be manufactured with the ring-like elastic belt 174 and provided to consumers in a configuration wherein the front waist region 116 and the back waist region 118 of the chassis 102 are connected to each other as packaged, prior to being applied to the wearer. As such, diaper pants may have a continuous perimeter waist opening 176 and continuous perimeter leg openings 178 such as shown in FIG. 2A.

The ring-like elastic belt 170 may be defined by a first elastic belt 172 connected with a second elastic belt 174. As shown in FIGS. 2A-2C, the first elastic belt 172 extends between a first longitudinal side edge 180*a* and a second longitudinal side edge 180*b*. And the second elastic 174 belt extends between a first longitudinal side edge 182*a* and a second longitudinal side edge 182*b*. The distance between the first longitudinal side edge 180*a* and the second longitudinal side edge 180*b* defines a pitch length, PL, of the first elastic belt 172, and the distance between the first longitudinal side edge 182*a* and the second longitudinal side edge 182*b* defines the pitch length, PL, of the second elastic belt 174. The first elastic belt 172 is connected with the first waist region 116 of the chassis 102, and the second elastic belt 174 is connected with the second waist region 118 of the chassis 102. As shown in FIGS. 2A-2C, opposing end regions of the first elastic belt 172 are connected with opposing end regions of the second elastic belt 174 at a first side seam 184 and a second side seam 186 to define the ring-like elastic belt 170 as well as the waist opening 176 and leg openings 178. It is to be appreciated that the ring-like elastic belt may be formed by joining a first elastic belt to a second elastic belt with permanent side seams or with openable and reclosable fastening systems disposed at or adjacent the laterally opposing sides of the belts.

As previously mentioned, absorbent articles may be assembled with various substrates that may be inspected during assembly. Thus, in the context of the previous discussion, the apparatuses and methods herein may be used to inspect substrates and components during the manufacture of an absorbent article 100 to detect various characteristics, such as for example, wrinkles, missing components, and/or misplaced components. For example, the apparatuses and methods herein may be utilized to detect through holes in any of the topsheet 138; backsheet 136; absorbent core 140; leg cuffs 156; waist feature 158; side panels 104, 106, 108, 110; connection zones 168; fastening elements 162, 164, 166, and/or belts during the manufacture of an absorbent article 100. It is to be appreciated that the apparatuses and methods herein may detect the presence of, size, shape, location, orientation, and/or positions of holes in various substrates caused by various process operations carried out on the substrates during a manufacturing process, such as for example, high pressure bonding, the application of hot adhesives; ring-roll activation, and others.

Figure 3:
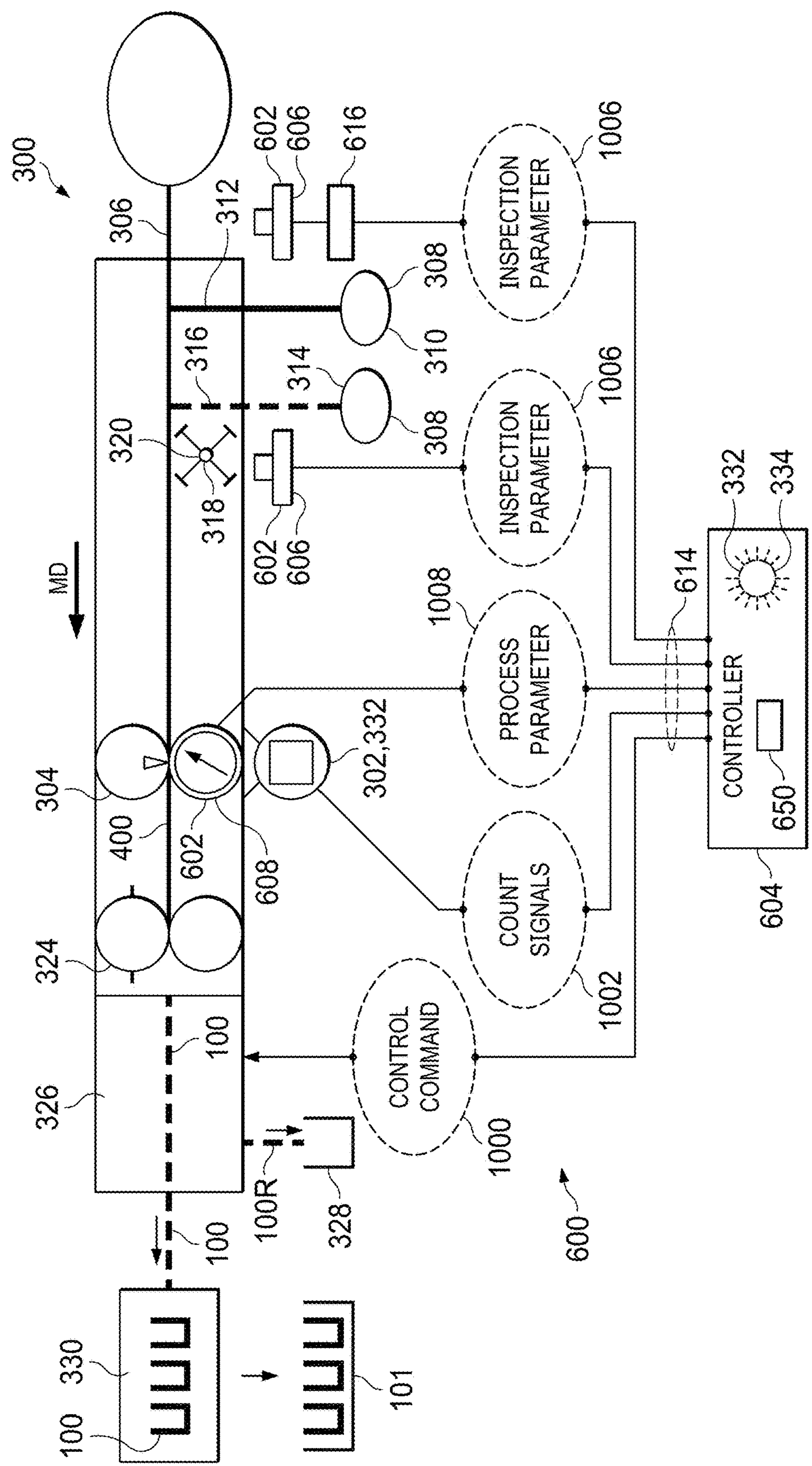
FIG. 3 is a schematic representation of an absorbent article converting line and control system.

FIG. 3 shows a schematic representation of an absorbent article converting process including a converting line or machine 300 configured to manufacture absorbent articles 100. It is to be appreciated that the systems and methods disclosed herein are applicable to work with various types of converting processes and/or machines. As shown in FIG. 3, the converting line 300 may include one or more motors 302 that drive transport systems, such as a nip roll 304, to move diaper substrates and component materials through the manufacturing process. For example, FIG. 3 shows a base substrate 306 and two auxiliary substrates and/or components 308 of material used to construct portions of the diapers. The substrates may be provided as rolls and fed into the converting line 300. It is to be appreciated that material of the auxiliary substrates may be supplied in various ways. For example, FIG. 3 shows a first auxiliary substrate 310 in the form of a continuous substrate 312, and a second auxiliary substrate 314 in the form of individual components 316. It is to be appreciated that the auxiliary substrates 310 may be transferred to the base substrate through various types of transfer mechanisms. For example, the individual components 316 may be in the form of side panels 104, 106, 108, 110 such as shown in FIG. 1A. As such, the side panels 104, 106, 108, 110 may be transferred to the base substrate via a transfer mechanism 318 in the form of a servo patch placer mechanism 320, such as disclosed in U.S. Pat. Nos. 6,450,321; 6,705,453; 6,811,019; and 6,814,217. In addition, the nip roll 304 may be configured create bonds between the side panels 104, 106, 108, 110 and the chassis 102. For example, the nip roll 304 may be configured as a mechanical bonding unit, such as disclosed in U.S. Pat. No. 4,854,984. In another example, the nip roll may be configured as a thermal bonding unit such as disclosed in U.S. Pat. No. 6,248,195. It is also to be appreciated that the various substrates can be used to construct various components of the absorbent articles, such as backsheets, topsheets, ears, leg cuffs, elastic waist features, and absorbent cores. Exemplary descriptions of absorbent article components are provided above with reference to FIGS. 1A and 1B.

Referring still to FIG. 3, as the base substrate 306 advances through the converting line 300, the base substrate 306 is combined with the auxiliary substrates 308 and/or discrete components 316 to create a continuous length of absorbent articles 400. At a downstream portion of the converting process 300, the continuous length of absorbent articles 400 is subjected to a final knife 324 and cut to create separate and discrete absorbent articles 100 in the form of diapers. Defective articles 100R may be subject to a rejection system 326 and removed from the process. For example, FIG. 3 shows defective articles 100R being channeled to a reject bin 328. It is to be appreciated that the term "reject bin" is used herein generically to designate the location where rejected diapers may be conveyed. As such, the reject bin 328 may include various systems. For example, the reject bin 328 may include additional systems such as conveyors and/or pneumatic systems to provide additional transport or conveyance of rejected diapers to other locations. Articles 100 that are not deemed to be defective may be subject to further processing steps, such as folding and packaging. For example, FIG. 3 shows diapers 100 advancing from the final knife 324 to a packaging system 330 and placed into packages 101.

As shown in FIG. 3 an inspection system 600 may be configured to interact with, monitor, and/or control the converting line 300. Various sensors 602 and other devices may be arranged adjacent to the converting line 300 may communicate with a controller 604. As described in more detail below, a convolutional neural network 650 associated with the controller 604 can be utilized to process the communications received from the various sensors 602. Based on the processing of such communications, the controller 604 may monitor and affect various operations on the converting line 300. For example, the controller may send various types of control commands 1000 to the converter line, such as disclosed, for example, in U.S. Pat. Nos. 8,145,338; 8,145,344; and 8,145,343. In some configurations, the control commands 1000 may be in the form of reject commands communicated to the reject system 326.

It is to be appreciated that the controller 604 and associated convolutional neural network 650 may be configured in various ways. For example, the controller 604 may be in the form of a personal computer (PC), a central processing unit (CPU), a field programmable gate array (FPGA), an application specific integrated circuit (ASIC), or a graphical processing unit (GPU). Example hardware with FPGAs may include the National Instruments PCIe-1473R, National Instruments PXIe-1435, National Instruments 1483R with FlexRIO FPGA module, or individual FPGA devices from the Altera Stratix, Altera Cyclone, Xilinx Spartan, or Xilink Vertexseries. GPU examples may include devices from nVidia platforms such as the Titanseries, GeForce GTX7 through 11 series, Quadro or Jetson series, or from AMD's Radeon HD, R, and RX series.

It is to be appreciated that the controller 604 may also be configured to communicate with one or more computer systems, such as for example, a programmable logic controller (PLC), programmable automation controller (PAC), and/or personal computer (PC) running software and adapted to communicate on an Ethernet/IP network, or using one or more other suitable network protocols, such as USB, FireWire and CameraLink. Some configurations may utilize industrial programmable controllers such as the Siemens S7 series, Rockwell ControlLogix, SLC or PLC 5 series, or Mitsubishi Q series. The aforementioned configurations may use a personal computer or server running a control algorithm such as Rockwell SoftLogix or National Instruments Labview or may be any other device capable of receiving inputs from sensors, performing calculations based on such inputs and generating control actions through servomotor controls, electrical actuators or electro-pneumatic, electro-hydraulic, and other actuators. Process and product data may be stored directly in the controller or may be located in a separate data historian. In some configurations, the historian is a simple data table in the controller, in other configurations, the historian may be a relational or simple database. Common historian applications include Rockwell Automation Factory Talk Historian, General Electric Proficy Historian, OSI PI, or any custom historian that may be configured from Oracle, SQL or any of a number of database applications. In some configurations, and as described in more detail below, the process and product data may include images that are collected by the sensors that can be subsequently utilized as training images when determining convolutional neural network parameters for a convolutional neural network 650. It is also to be appreciated that the controller 604 may be configured to communicate with various types of controllers and inspection sensors configured in various ways and with various algorithms to provide various types of data and perform various functions, for example, such as disclosed in U.S. Pat. Nos. 5,286,543; 5,359,525; 6,801,828; 6,820,022; 7,123,981; 8,145,343; 8,145,344; and 8,244,393; and European Patent No. EP 1528907 B1, all of which are incorporated by reference herein.

As the substrates and components travel in the machine direction (MD) through the converting line, the controller 604 tracks the advancement of the substrates and components. In some configurations such as shown in FIG. 3, the controller 604 may track the advancement with counts generated by a machine axis 332 that correspond with machine direction positions on substrates and components while advancing though the converting line 300. In some configurations, the machine axis 332 may be configured as an actual motor 302 that provides count signals 1002 to the controller 604. The controller 604 may utilize rotational speed, time, and/or count data from the machine axis 332 that correspond with the machine direction speed and travel of the substrates and components through the converting line 300.

It is to be appreciated that instead of or in addition to utilizing feedback from a physical machine axis as discussed above, the rotational motion of the machine axis 332 may be simulated by software in the controller. For example, in FIG. 3, the controller 604 can utilize counts generated by a virtual machine axis 334 in the controller software. More particularly, the virtual machine axis 334 may be programmed to imitate a motor that generates counts as the motor rotates. As such, it is to be appreciated that the machine axis 332 referred to herein may be either a virtual axis existing in software or a physical axis corresponding with the rotational motion of a motor or other equipment.

Figure 4:
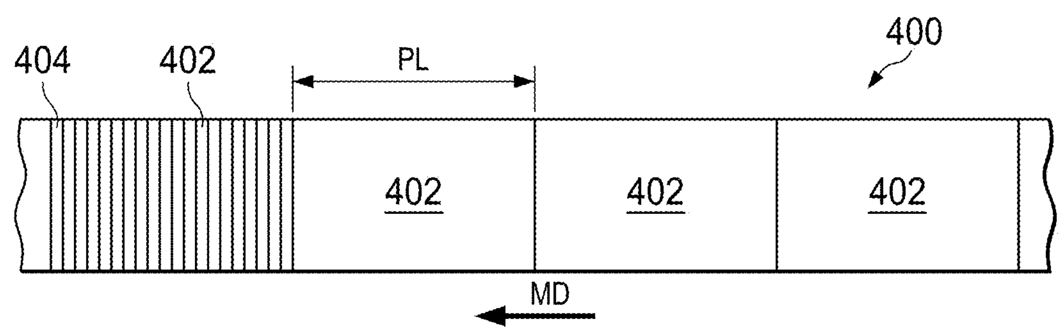
FIG. 4 is a top view of an advancing substrate showing virtual products and virtual segments.

As discussed above, the machine axis 332 may be configured to correlate the linear motion of the substrates and components in the machine direction through the converting line 300 with counts corresponding with rotation of the machine axis 332. In some configurations, one complete rotation of the machine axis 332 and associated count data correspond with one pitch length of an absorbent article 100. In some configurations, the pitch lengths of the absorbent articles are the machine direction longitudinal lengths of the individual absorbent articles being produced. FIGS. 1A and 1B show an example of a longitudinal pitch length PL of a diaper. As such, the controller 604 may use counts generated from the machine axis 332 to virtually divide the substrates and components into virtual products 402. As shown in FIG. 4, the virtual products 402 may have machine direction lengths PL that correspond with the pitch lengths PL of products being produced. For example, FIG. 4 shows a top view of the base substrate 306 divided into virtual products 402 along the machine direction by the controller 604. Count signals corresponding with rotation of the machine axis that correspond with less than a complete rotation can also be used by the controller to divide each virtual product 402 into virtual segments 404, such as shown in FIG. 4. As discussed in more detail below, the substrate speed and estimated clock inaccuracies can be used to determine the length of each virtual segment in the machine direction, and in turn, the number of virtual segments in each virtual product. For example, FIG. 4 shows one virtual product 402 divided into twenty virtual segments 404. As discussed in more detail below, the controller 604 can also utilize signals from the sensor 602 that correspond with the detection of various parameters in virtual products and segments to correlate the locations of parameters within manufactured products 100 based on processing of the signals by the convolutional neural network 650. It is also to be appreciated that the controller 604 may be configured to correlate inspection results and measurements from an absorbent article converting process using any of a variety of suitable techniques, such as those disclosed in U.S. Pat. No. 8,145,338, which is incorporated by reference herein.

As previously mentioned, the systems and methods herein utilize various types of sensors 602 to monitor the substrates and components traveling through the converting line. As shown in FIG. 3, sensors 602 may be configured as inspection sensors 606 to monitor various aspects in the substrates and/or components being processed by the converting line or machine 300. In some configurations, the inspection sensors 606 may be used to assist with the detection of defects within substrates and/or components themselves, such as for example, damage, holes, tears, wrinkles, and the like, and may also be used to assist with the detection of defective assemblies and/or combinations of the substrates and components, such as for example, missing and/or misplaced ears, landing zones, fasteners, and the like. The inspection sensors 606 may be used to assist with the detection of contaminants, such as foreign material, grease, or dirt. As such, inspection sensors 606 may be configured to assist with the detection of the presence or absence of substrates and/or components, and may be configured to assist with the detection of the relative placement of substrates and/or components. As discussed in more detail below, feedback signals from the inspection sensors 606 in the form of inspection parameters 1006 are communicated to the controller 604 for processing by an inspection algorithm of the convolutional neural network 650. In some configurations, for instance, the inspection parameters 1006 include images of the base substrate 306, the auxiliary substrates 308, discrete components 316, and so forth. In some configurations, such images can be collected by the inspection sensors 606 without needing to illuminate the area of inspection with light with required specific wavelengths, such as infrared light and/or ultraviolet light. Additionally or alternatively, the inspection parameters 1006 can include other forms of data, such as digitized signals, that can be processed by the inspection algorithm of the convolutional neural network 650.

It is to be appreciated that various different types of inspection sensors 606 may be used to monitor substrates and various components while advancing through the converting line 300. For example, inspection sensors 606 may be configured as photo-optic sensors that receive either reflected or transmitted light and serve to determine the presence or absence of a specific material; metal-proximity sensors that use electromagnetic to determine the presence or absence of a ferromagnetic material; or capacitive or other proximity sensors using any of a number of varied technologies to determine the presence, absence, or thickness of materials. In some configurations, the inspection sensors 606 may also be configured as vision systems and other sub-processing devices to perform detection and, in some cases, logic to more accurately determine the status of an inspected product. Particular examples of such inspection sensors 606 may include the Sick PS30 pattern sensor, Keyence AI series pattern matching sensor, Cognex Insight cameras, DVT Legend or Keyence smart cameras, component vision systems such as National Instruments PXI or PC based vision system such as Cognex VisionPro or any other vision system software which can run on a PC platform. It should also be appreciated that inspection parameters 1006 may be provided from inspection sensors 606 in various forms. In one configuration, inspection parameters 1006 may be in the form of images or other types of signals which are processed by the convolutional neural network 650 to determine the presence or absence of a particular defect, feature and/or other component. Such images or signals may also be stored in any suitable data store, such as, for example, a database or in a specified directory on an image server for offline processing in the refinement of the inspection algorithm of the convolutional neural network 650, as described below. Such images or signals can be transferred via a standard protocol such as ftp (File Transfer Protocol), GigE, 10 GbE, TCPIP, USB, CameraLink, CoaXpress, Thunderbolt, N-BaseT, 10G Base-T, HD-SDI. NFS (network file system), SMB (Server Message Block), DDE (Dynamic Data Exchange), or OPC (Object Linking and Embedding for Process Control).

The systems and methods herein utilize various types of sensors 602 or data from the controller 604 to monitor the various assembly equipment used in the converting line 300. As shown in FIG. 3, equipment sensors 602 may be configured as process sensors 608 to monitor various aspects of process equipment or operations. In some configurations, the process or equipment sensors may be linear position transmitters, rotary position transmitters, rotational encoders for speed and position feedback, temperature sensors such as RTD elements, pressure and/or vacuum transmitters or vibration sensors. Controller data may be configured as data from drive position or velocity control loops, automatic or operator induced control actions, motor current or power or any other parameter that can be harvested from a controller 604. Based on the detections of the process sensors 608, feedback signals from the process sensors 608 in the form of process parameters 1008 are communicated to the controller 604.

As shown in FIG. 3, the sensors 602, such as the inspection sensors 606 and process sensors 608, may be connected with the controller 604 and historian through a communication network 614, which allows the inspection sensors 606 and process sensors 608 to communicate inspection parameters 1006 and process parameters 1008, respectively, to the controller 604. As discussed in more detail below, devices that communicate on the network each include precision clocks that are synchronized to a master clock within some specified accuracy. As shown in FIG. 3, the sensors 602 and the controller 604 may be connected directly with the communication network 614. As such, each sensor or other field device connected directly with the communication network may include a clock. Sensors 602 that include a clock and that may be connected directly with the communication network 614 may include, for example, vision systems such as National Instruments CVS or any PC-based vision system such as Cognex VisionPro. Such sensors may also include other controllers that may be configured as peers to the controller or may be configured as subordinate to the controller.

In some configurations, the sensors 602, such as the inspection sensors 606 and process sensors 608, may be indirectly connected with the communication network 614. For example, the inspections sensors 602 may be connected with the communication network 614 through a remote input and output (I/O) station 616. When utilizing remote I/O stations 616, the sensors 602 may be hardwired to the remote I/O stations, and in turn, the remote I/O stations are connected with the communication network 616. As such, each remote I/O station 616 may include a precision clock. Example remote I/O stations 616 or other IEEE-1588 based instruments that can be utilized with systems and methods herein include, for example a National Instruments PCI-1588 Interface (IEEE 1588 Precision Time Protocol Synchronization Interface) that synchronizes PXI systems, I/O modules and instrumentation over Ethernet/IP or a Beckhoff Automation EtherCat and XFC technology (eXtreme Fast Control Technology).

As previously mentioned, each device, such as the inspection sensors 606 and process sensors 608, remote I/O stations 616, and the controller 604, connected with the communication network 614 includes a clock, and each clock is synchronized to a master clock. In one configuration, the controller 604 includes the master clock, and all other clocks of devices connected with the communication network are referenced to the controller master clock. In such a configuration, the remote I/O stations, inspection sensors, and process sensors each include a clock that is synchronized to the controller master clock. For example, inspection parameters 1006 provided by the inspection sensors 606 and process parameters 1008 provided by the process sensors 608 communicated to the communication network 614 are time-stamped with the time from the clocks on the corresponding sensors and remote I/O stations. In turn, the inspection parameters and process parameters, and corresponding time-stamp data are sent to the controller 604 over the communication network 614. Thus, the controller 604 can be programmed to correlate the inspection parameters and process parameters based on the actual time the parameters were provided by the respective sensors. Therefore, ambiguity as to when detections were actually made by respective sensors is relatively small. Additionally, traditional methods of storing inspection parameters and process parameters normally rely on OPC (Object Linking and Embedding for Process Control) to pass data which is subsequently time-stamped at the destination, for example, a computer housing the historian. With these methods, the transport delays between the data source and the clock drift of the computer housing the historian combine to create further ambiguity in the detection time-stamp of the data.

The controller may 'normalize' the time-stamps by adjusting the reported time-stamps which were recorded at the time of detection to a reference location in the process. In this manner, all data may be correlated to the production time (normalized time) of the particular product on which the measurement was detected. For example, if an inspection is performed using an inspection system 600, which may include a vision system utilizing an inspection algorithm of the convolutional neural network 650, at some location in the process, and equipment parameters are recorded by a process sensor 602 at a second location in the process, the controller may adjust each time-stamp in such a way that all parameters will have the same time-stamp and therefore be correlated to the same individual product. Further, if some product is removed from the production in order to perform offline manual inspections, the system can be configured to record the sample time of the product being removed, to adjust that time-stamp to the normalized time of that individual product and to present that time-stamp to the quality assurance laboratory, who may use that time-stamp when that data is stored in the historian. By recording the time-stamp at the moment of detection, normalizing it to a reference point in the process and passing the normalized time-stamp to the historian as the associated data time-stamp, the majority of the ambiguities in the system are eliminated.

All clocks that are used to determine and report time-stamps may be synchronized together. Clock synchronization allows the reported time from one device on the communication network 614 to be utilized by another device on the communication network. When the clocks are synchronized, ambiguity as to when parameters were actually provided by the respective sensors 602 is affected only by the accuracy of the clocks with respect to each other. The clocks of the devices on the communication network may be synchronized in various ways depending on the type of communication network 614 used.

In one configuration, the communication network 614 is configured as a non-deterministic communication network, such as for example, Ethernet or Ethernet IP (industrial protocol) communication network. When using an Ethernet IP communication network, the clocks of each device may be synchronized using the IEEE1588 precision time protocol, described in IEEE1588 Standard, "Precision Clock Synchronization Protocol for Networked Measurement and Control Systems" and also described in Rockwell Automation publication number 1756-WPO05A-EN-E, published January 2009, and entitled "An Application of IEEE 1588 to Industrial Automation." Alternatively, when using an Ethernet communication network, the clocks of each device may be synchronized via time sensitive networking (TSN) protocols as described by the standard IEEE 802.1AS-2011, "IEEE Standard for Local and Metropolitan Area Networks—Timing and Synchronization for Time-Sensitive Applications in Bridged Local Area Networks." As mentioned above, time-stamps associated with parameters from any sensor may be referenced to the master clock, which allows the relative time as to when the inspection parameters were provided to be accurately calculated. In one configuration, the controller includes the master clock, the controller master clock, and all other clocks of devices connected with the communication network, the sensor clocks, are referenced to the controller master clock. As a result, the time as to when inspection parameters, process parameters, and identifier parameters were provided from respective sensors can be can be reported to the controller within the accuracy of a standards compliant clock. In some configurations, reported time-stamps may be accurate to within 0.1 milliseconds of the controller master clock. In another configuration, another device, such as an Ethernet switch or router is the local master clock. In this case, both the controller clock and the sensor clock follow the local master clock. The identity of the local master is unimportant since all clocks in the system are synchronized to the local master within the standard.

With reference to the above description and figures, the methods and systems herein utilize a controller 604 and one or more sensors 602, such as inspection sensors 606 and process sensors 608, connected with a communication network 614. Each sensor 602, and remote I/O device 616, if used, have clocks that are synchronized with the master controller clock in the controller. The controller 604 tracks the movement of the substrates and components traveling in the machine direction of the converting line 300. More particularly, controller 604 utilizes feedback from the machine axis 332 to virtually divide the substrates and components into virtual products 402 along the machine direction, track the movement of virtual products 402 in the machine direction, and correlate the virtual products 402 to actual individual products 100 produced after being cut by the final knife 324. In addition, the controller 604 utilizes feedback from the machine axis 332 to virtually divide the virtual products 402 into virtual segments 404 along the machine direction.

During manufacture, the inspection sensors 606 provide inspection parameters 1006 to the controller 604 via the communication network 614. As discussed above, the inspection parameters 1006 can be configured to indicate various types of information, such as measurement data and/or images, about the substrates and/or components. The inspection sensors 606 can provide inspection parameters 1006 to the communication network along with associated time-stamp from the sensor clocks. Similarly, the process sensors 608 can provide process parameters 1008 to the controller 604 via the communication network 614. As discussed above, the process parameters 1008 can be configured to indicate various types of information, such as temperatures and/or pressures, from the assembly equipment on the converting line 300. In turn, the process sensors 608 provide process parameters 1008 to the communication network along with associated time-stamp from the sensor clocks. The controller 604 receives the inspection parameters 1006 and process parameters 1008, and associated time-stamps from the communication network 614 and correlates the inspection parameters 1006 and process parameters 1008 with the corresponding virtual products 402 and/or virtual segments 404 moving along the converting line 300, and in turn, with individual products 100 in a package 101.

It should be noted that while time-stamps, and specifically normalized time-stamps are an efficient method to provide correlation between process data, inspection parameters and product performance feedback, other techniques to make the correlation may be used. For example, a product's unique identifier may be a mathematical sequence. The controller 604 and inspection devices 616 may independently generate the same sequence. When data is stored from varied sources, each piece of data is identified by the product unique identifier rather than a time.

As described in more detail below, based on the inspection algorithm of the convolutional neural network 350, the controller 604 may be adapted to send various types of control commands 1000 to the converting line 300, such as for example, speed change commands, reject commands, and shutdown commands. Additionally or alternatively, the control commands 1000 can causes various control actions, such as an automatic phase adjustment, an automatic tracking adjustment, a machine maintenance scheduling, and machine stop commands. Such control commands 1000 may be based on parameters communicated from various sensors 602 as described above. For example, control commands 1000 may be based on images included in the inspection parameters 1006 and/or process parameters 1008 provided by inspection sensors 606 and process sensors 608.

Figure 5:
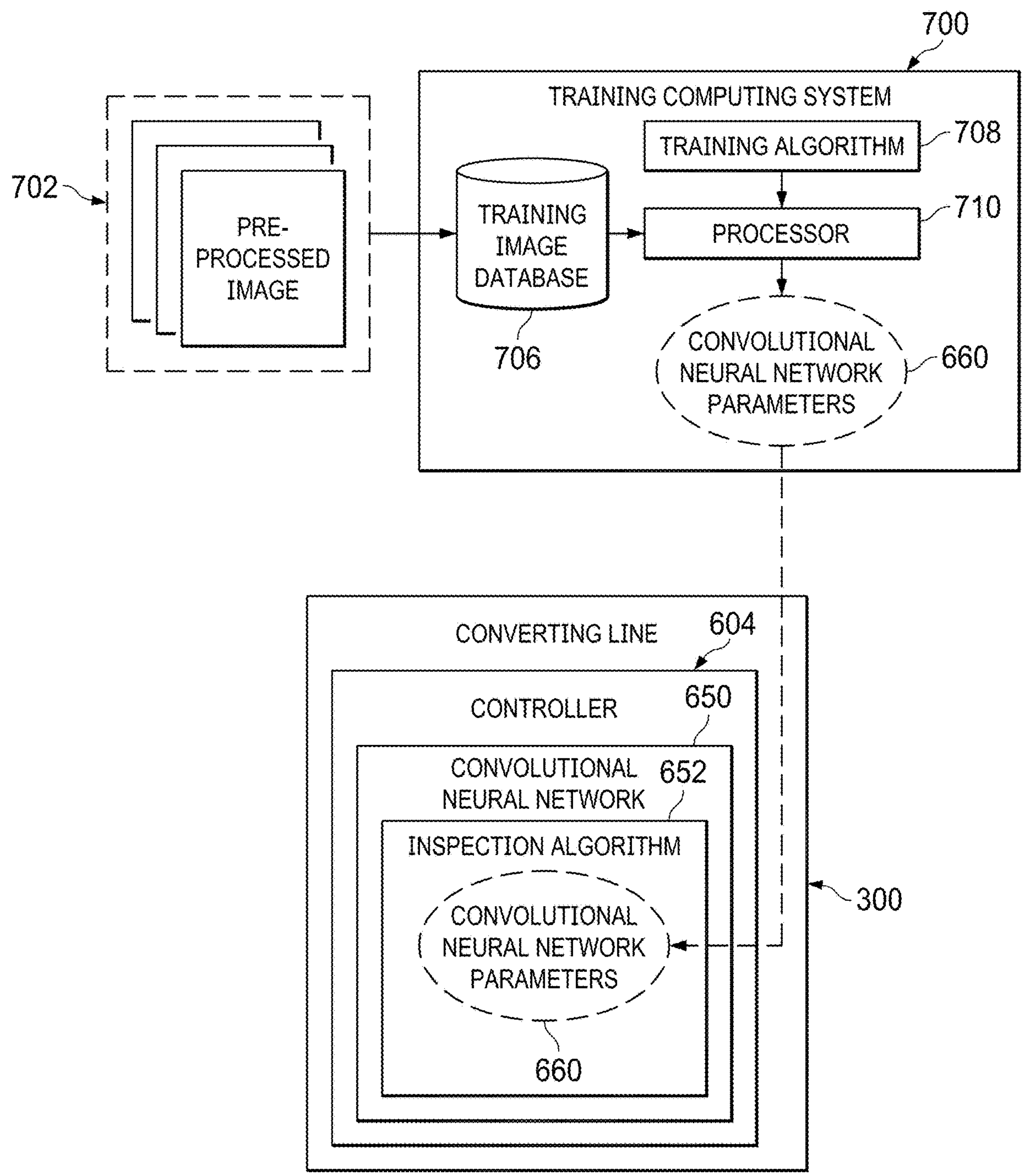
FIG. 5 is a block diagram of a convolutional neural network learning paradigm for determining convolutional neural network parameters for an inspection algorithm of a convolutional neural network for converting line inspection.

The convolutional neural network 650 can comprise one or more convolutional layers, activation layers and pooling layers, followed by one or more fully connected layers as in a standard multilayer neural network. The convolutional neural network may also be made fully convolutional by not including a fully connected layer. In order for the convolutional neural network 650 to process the images, or other data, collected by the sensors 602, a learning paradigm is utilized to determine convolutional neural network parameters for an inspection algorithm. Once the parameters have been determined, the convolutional neural network can be used in production to produce results independently using the inspection algorithm. FIG. 5 is a block diagram of a convolutional neural network learning paradigm for determining convolutional neural network parameters 660 for an inspection algorithm 652 of a convolutional neural network 650 for converting line inspection. Training can take on many different forms, using a combination of learning paradigms, learning rules, training frameworks, and learning algorithms, which are schematically represented as training algorithm 708 in FIG. 5. The training algorithm 708 can be executed by a processor 710 of a training computing system 700. In this configuration, a static network is utilized, as the learning phase is distinct from the production phase. As described in more detail below, however, once the convolutional neural network is deployed into production, additional learning/training can be utilized (i.e., offline from production) to fine-tune, calibrate, or otherwise adjust the convolutional neural network parameters. The convolutional neural network can then be updated with the refined parameters to improve performance of the inspection algorithm.

The learning paradigm for determining a set of convolutional neural network parameters 660 shown in FIG. 5 is based on the analysis of images in a training image database 706. In the illustrated example, the images stored in the training image database 706 can include a multitude of images of collected from one or more converting lines 300 during production of absorbent articles 100 (FIGS. 1A and 1B). The images in the training image database 706 can be tagged or otherwise grouped into training sets, such that each image has a label corresponding to the result that an inspection algorithm is expected to match. For ease of illustration, the images of the training image database 706 are shown to include a set of preprocessed images 702. As such, each of the images 702 in the training image database 706 can include a labeled component that is of interest for quality control purposes. The labeled component can be, for instance, a feature, aspect, or attribute of the absorbent article that is marked and tagged as such. The labeled components can be components that are desired to be present or components that are undesirable to be present. For instance, the labeled component may mark the landing zone of each image 702 or may mark a wrinkle, tear, or folded component in each image 702.

With specific regard to landing zones, as an example, detection of absorbent article landing zones using traditional machine vision tools presents challenges. For instance, landing zones may have generally low contrast and positioned within areas of busy artwork. Such arrangements can be challenging for traditional machine vision tools, as the artwork may be identified as an edge of the landing zone, while the actual edge of the landing zone is overlooked. In accordance with the present disclosure, however, each of the preprocessed images 702 can have the landing zones labeled such that the inspection algorithm can learn to identify the landing zone with a much higher degree of accuracy.

Component labeling can be performed using any suitable process or technique, such as through human determination, by an artificial intelligence algorithm, a traditional detection algorithm (i.e., non-artificial intelligence), or other resource intensive, high accuracy detection algorithm, for example. Furthermore, while images are depicted as the data set in FIG. 5, this disclosure is not so limited. Instead, any data set can be provided to the training algorithm 708 that is based on data that can be collected and digitized by the sensors 602 during the manufacturing process for processing by the inspection algorithm 652. In this regard, example data sets useable to train the convolutional neural network 650 can include, without limitation, a 3-D point cloud, height maps, density data, opacity data, aural data, profile signals, sensor data, and so forth.

Once the training computing system 700 has applied the training algorithm 708 to the images in the training image database 706, the convolutional neural network parameters 660 can be generated. Example parameters can include, without limitation, the number of convolutional layers, the number of neurons per layer, the number of pooling layers, the weights connecting different layers, number of drop out layers, and so forth. The convolutional neural network parameters 660 can then be implemented as an inspection algorithm 652 of the convolutional neural network 650 associated with a converting line 300. Based on the determination of the inspection algorithm 652 of the convolutional neural network 650 control commands 1000 can be sent to the to the converting line 300, as may be needed.

Figure 9:
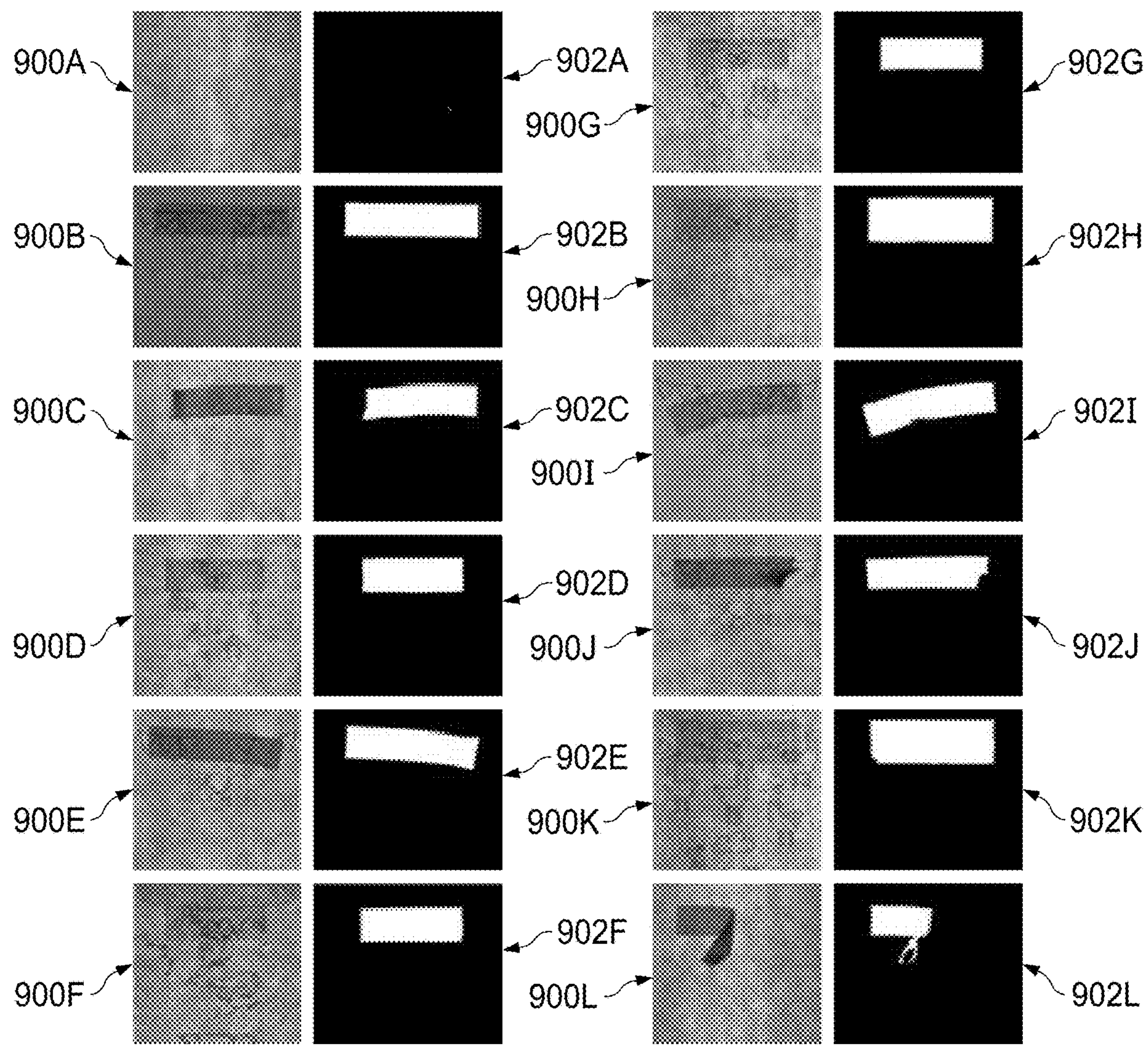
FIG. 9 shows an example set of images from a converting line in which the landing zone has been identified in accordance with the present disclosure.

Referring to FIG. 3, the inspection parameters 1006, such as images, received from the sensors 606 can be processed by the inspection algorithm 652 to identify the labeled component in each of the absorbent article 100. By way of example, if the labeled component is a landing zone, the landing zone of each absorbent article 100 can be identified in the images using the inspection algorithm 652. In some configurations, the images collected from the converting line 300 can be processed using the inspection algorithm 652 such that the landing zone is identified as white pixels while the remaining pixels of the image are black. For the purposes of illustration, FIG. 9 shows an example set of images from a converting line in which the landing zone has been identified in accordance with the present disclosure. Images 900A-L are images collected by a sensor, such as sensor 602 shown in FIG. 3. The images 900A-L may be processed by an inspection algorithm, such as inspection algorithm 652, to produce the corresponding images 902A-L. The landing zones in the corresponding images 902A-L, if present, are identified as white pixels. While FIG. 9 depicts images related to the detection of a single component (i.e., a landing zone), in other configurations multiple components can be labeled for identification. For such cases, a collection of masked images may be produced with each image labeling one of the multiple components using black and white pixels, as shown in FIG. 9. Alternatively, instead of utilizing multiple images, a single output image can be generated with the different components separated out on different color channels of the image. Such images may then be analyzed directly or separated into individual images from each channel for analysis.

Again referring to FIG. 9, with the landing zone identified as white pixels, image analysis can then be performed using a second inspection algorithm to determine certain properties of the component. Based on the properties, it can be determined whether the landing zone satisfies certain quality control parameters. While the properties of the labeled component will vary based on the labeled component that is identified in the images, in the instance of a landing zone, the properties may be the total area of the landing zone, machine and cross machine position of the landing zone, and the angular orientation of the landing zone. By way of example, if the total area of the landing zone is determined to be less than a threshold, the landing zone is outside of a desired position envelope, and/or the angular orientation of the landing zone exceeds a certain threshold, the absorbent article can be deemed to be defective. Referring to image 902I of FIG. 9, the landing zone identified in that image may exceed the angular orientation threshold. The position of the landing zone identified in image 902H may be too close to the image boundary. The area of the landing zone identified in image 902L may be less than the threshold landing zone area. In all instances, the associated absorbent article associated with those images may be rejected based on the assessment of the second inspection algorithm.

While the images 900A-L show example processing a landing zone, it is to be appreciated that a wide variety of labeled components can be identified using the systems and methods disclosed herein. For instance, the labeled component may be contaminants such as a foreign material, grease, or dirt, or results of an undesired transformation of the absorbent article, such as a hole, tear, or wrinkle. The image showing the labeled component can be processed such that the labeled component is presented as white pixels, with the remaining pixels of the image being black. Based on the properties of the labeled component (presence, absence, total number, length, width, texture, size, position, orientation, etc.), as may be determined through image analysis, various processing decisions can be made.

Figure 6:
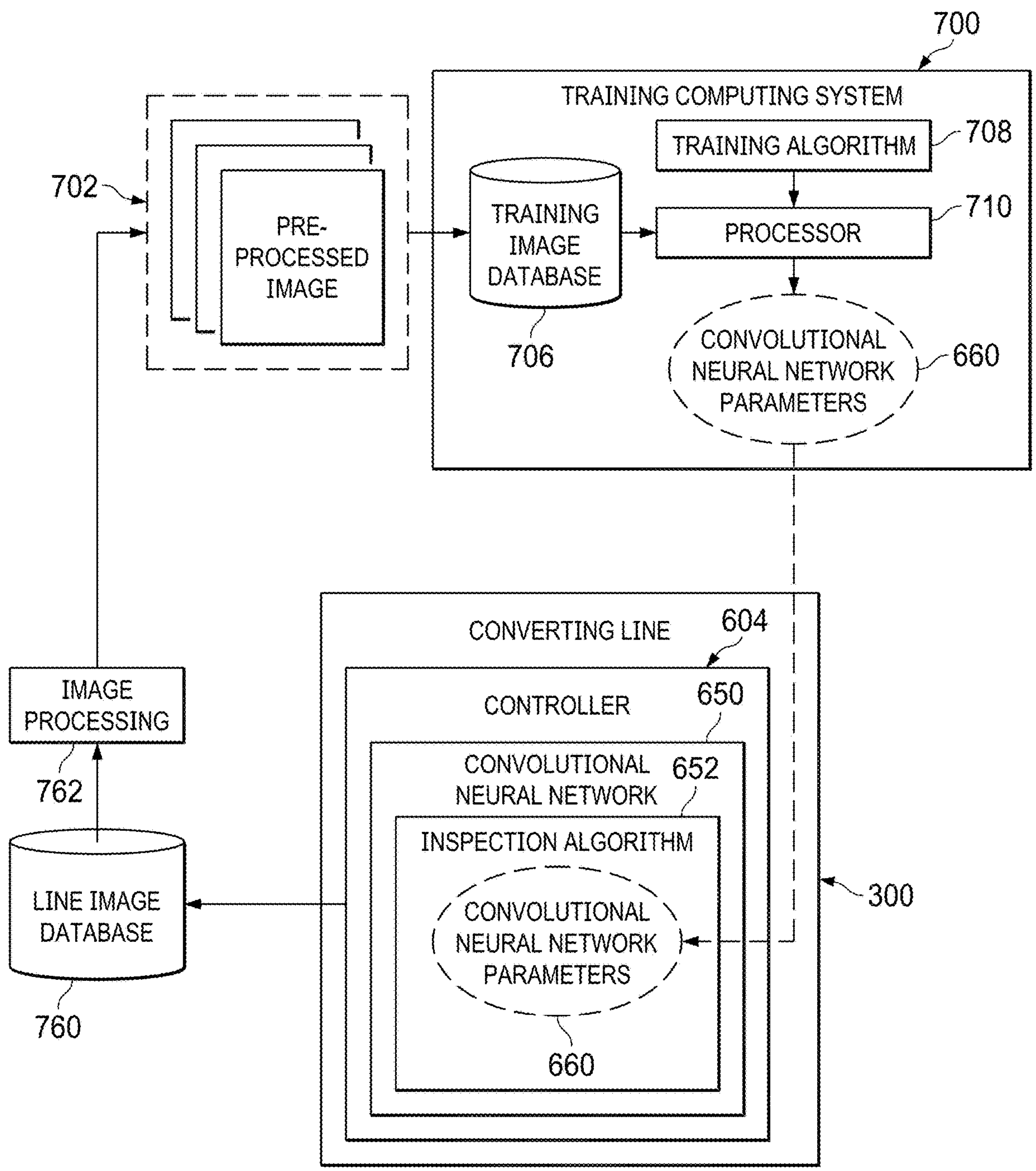
FIG. 6 is a block diagram of a convolutional neural network learning paradigm for determining convolutional neural network parameters for an inspection algorithm utilizing a feedback control loop from a converting line.

Referring now to FIG. 6, a block diagram of a convolutional neural network learning paradigm for determining convolutional neural network parameters 660 for an inspection algorithm 652 utilizing a feedback control loop from the converting line 300 is depicted. In this configuration, images of the training image database 706 include images of absorbent articles 100 collected by the sensors 606 of the converting line 300 (FIG. 3) during production and collected while a particular set of convolutional neural network parameters 660 is driving the inspection algorithm 652. In some configurations, the production-based images collected from the converting line 300 can be processed at an image processing function 762 to label images for utilization by the training algorithm 708. Notably, as the images stored in the line image database 760 are collected based on a particular set of convolutional neural network parameters 660, the efficiency of such parameters can be checked and verified by the feedback loop. Mischaracterizations or other processing issues can be considered by the training computing system 700 such that adjustments to the convolutional neural network parameters 660 can be determined by the training computing system 700. Once the convolutional neural network parameters 660 have be adjusted, they can be utilized by the inspection algorithm 652 to improve the accuracy and functionality of the inspection process.

With regard to visually detectable features or conditions of the absorbent article, the location of the feature or conditions in proximity to other visual stimulus may impact the visual perception to the consumer. More specifically, the location of the features or conditions may make them more obvious to an observer, or they may become more difficult to notice. For instance, the particular location of a defect or condition may impact whether the article should be rejected, as some defects or issues may not necessarily impact visual perception to such a degree that warrants the article being rejected. Therefore, in some configurations, the inspection algorithm 652 can be calibrated to identify the presence or absence of a certain defect, feature, or condition based on saliency modeling. As such, the inspection algorithm 652 can therefore be calibrated to reject articles only having defects, features, or conditions that impact the visual perception of the article. Beneficially, when utilizing saliency modeling, the large size (i.e., complexity) of the convolutional neural network 650 can be reduced. Reducing the number of layers of the convolutional neural network 650 can decrease processing time and can also reduce the computing resources necessary to execute the convolutional neural network 650.

Figure 7:
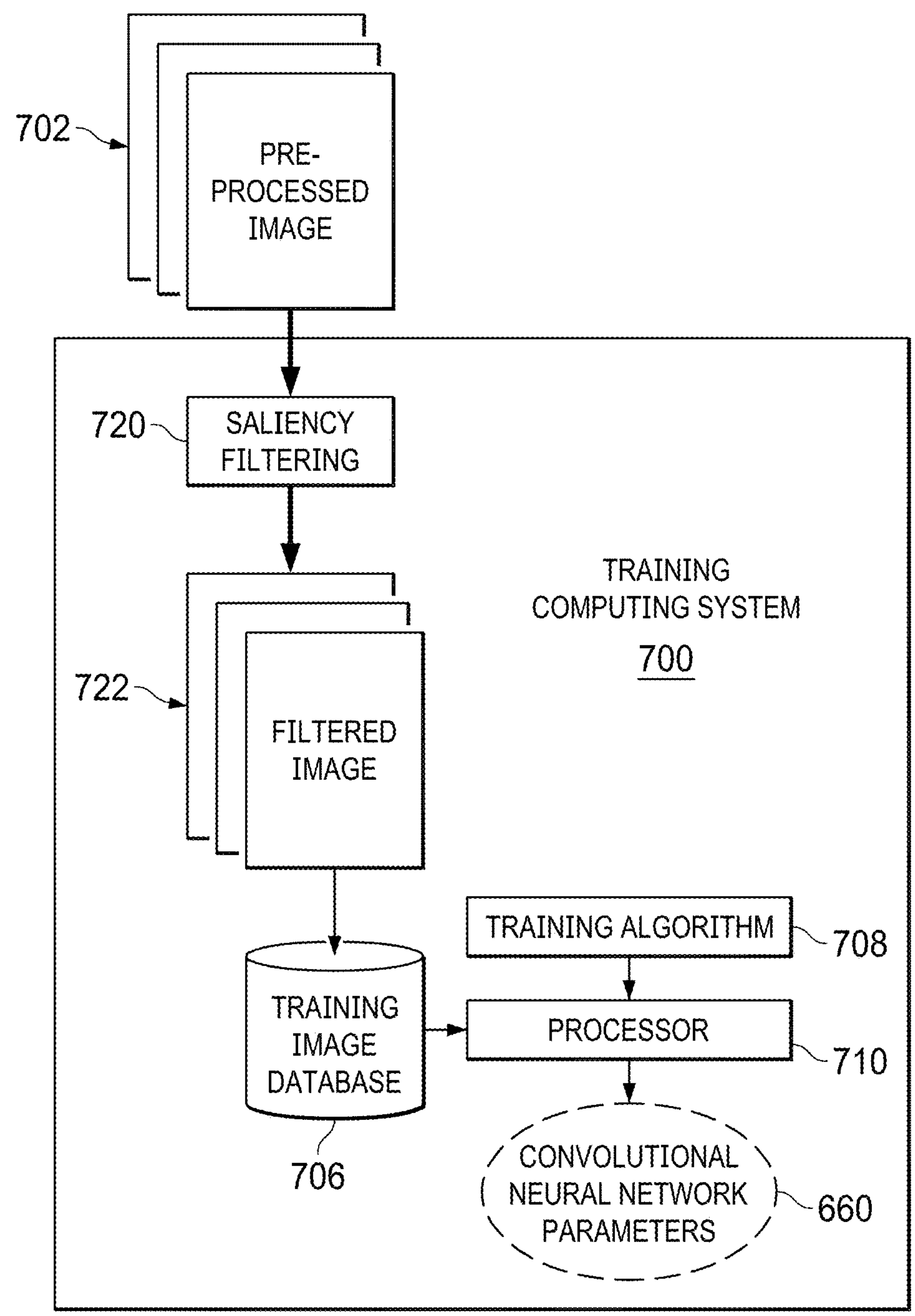
FIG. 7 is a block diagram of a convolutional neural network learning paradigm for determining convolutional neural network parameters utilizing saliency filtering to pre-process training images.

Referring now to FIG. 7, the training computing system 700 is depicted utilizing saliency filtering 720 to filter the pre-processed images 702 such that the training algorithm 708 will determine the convolutional neural network parameters 660 that take into account a consumer's visual perception of the defect or condition. Subsequent to the saliency filtering 720, the filtered images 722 can be stored in the training image database 706 and used by the training algorithm 708 to determine the convolutional neural network parameters 660.

The saliency filtering 720 can be performed using any suitable technique. In one example configuration, the saliency of the pre-processed images 702 is provided as additional channels to the input of the training algorithm 708. More specifically, the training algorithm 708 can provide the ability to train on color channel inputs, as opposed to just grayscale images. The saliency data of the pre-processed images 702 can be embedded in the filtered images 722 by creating a color image from a combination of the original grayscale image and the saliency heat-map. In accordance with one configuration, the saliency filtering 720 creates the filtered images 722 in the HSL (hue-saturation-luminance) color space which are then stored in the training image database 706. However, other color spaces, such as an RGB color space or a LAB color space, can be used. Using the HSL color space can ensure that the original grayscale data (i.e., pre-processed images 702) are fully recoverable from the color image (filtered images 722) without risk of inducing false saturation or false clipping during the conversion process. Using the HSL color space, the saliency filtering 720 can import the original grayscale pre-processed image 702 as the luminance channel, and the saliency map can be imported as the hue channel. The saturation channel can be set as a percentage of precept, where 100% saturation provides the full strength of the saliency input and 0% effectively ignores the saliency input. Utilizing a variable saturation channel beneficially allows certain regions of an image set to be masked (i.e., 0% saturation), if desired, so that only the remaining regions are considered by the training algorithm 708.

Providing saliency input to the training algorithm 708 can serve to reduce the number of convolutional layers the network has to train. Accordingly, the convolutional neural network parameters 660 are reduced, thereby allowing the convolutional neural network 650 (FIG. 5) to fit onto suitable hardware device(s) providing local and fast processing ability, such as a FPGA or the like.

Referring now to FIG. 8, in some implementations, the training computing system 700 can be positioned in a non-production environment 780. The non-production environment 780 can be in networked communication with one or more production environments 782, 784, 786 via a network 788. Each of the production environments can have one or more converting lines similar to the converting line 300 shown in FIG. 3. At certain intervals, or at an on-demand basis, updated convolutional neural network parameters 660 determined by the training computing system 700 can be transmitted to the various converting lines 300A-D via network communications in order to update or otherwise alter the inspection algorithm associated with those converting lines. For instance, the convolutional neural network parameters 660 can be written to the controllers implementing the inspection algorithm at the various converting lines. Thus, the converting lines 300A-D can be operated with a particular inspection algorithm while the training computing system 700 determines improved parameters for the associated convolutional neural network 650 (FIG. 5). Once determined, the convolutional neural network parameters 660 can be dispatched to the various remote converting lines 300A-D. Further, some or all of the converting lines 300A-D can supply some or all of the images 702 to the training computing system 700 in a feedback loop, as shown in FIG. 6. Thus, training images collectively received from many different converting lines 300A-D can be utilized by the training algorithm 708 to improve the convolutional neural network parameters 660. As is to be appreciated, the training computing system 700 positioned in a non-production environment 780 can utilize saliency filtering 720 (FIG. 7) to pre-process the images received from the converting lines 300A-D.

Converting lines utilizing convolutional neural networks described herein can provide for a variety of different inspection operations to discern consumer noticeable defects during the manufacturing process. Examples of features, flaws, defects, or other issues that can be detected using the systems and methods described herein include holes or tears in substrates, missing components, misplaced components, deformations of components, sufficiency of textures, bond location, bond appearance, and so forth. Various operational examples are provided below for illustration purposes.

In accordance with one non-limiting configuration, the inspection algorithm 652 of convolutional neural network 650 is used to discern the edge of a side panel 104 of an absorbent article 100 (FIGS. 1A and 1B) from bond patterns, graphics, textures, and other visual indicia that may be present during the inspection. Beneficially, the inspection algorithm 652 can determine whether the placement of the side panel 104 is acceptable with white light and without having to use light having a specific wavelength, such as infrared and/or ultraviolet light. In order to perform this type of inspection, a plurality of images 702 labeled as having proper placement of the side panel can be provided as an input to the training algorithm 708. In some implementations, the pre-processed images 702 can be filtered with saliency filtering 720, as described above. In any event, the training algorithm 708 then determines the convolutional neural network parameters 660 based on the pre-processed images 702. A convolutional neural network 650 utilizing the convolutional neural network parameters 660 can then process the inspection parameters 1006 from one or more sensors 602 to discern the placement of an edge of the side panel 104 during production.

In accordance with another non-limiting configuration, the inspection algorithm 652 of convolutional neural network 650 is used to detect an elastic strand so as to differentiate the elastic strand from a wrinkle. Similar to the above, such inspection can be performed in the presence of bond patterns, graphics, and other visual indicia that may cause confusion for other types of vision inspection systems. In order to perform this type of inspection, a plurality of pre-processed images 702 that label wrinkles can be provided as an input to the training algorithm 708. The pre-processed images 702 can be filtered with saliency filtering 720, as described above. The training algorithm 708 can then determine the convolutional neural network parameters 660 based on the pre-processed images 702. A convolutional neural network 650 utilizing the convolutional neural network parameters 660 can then process inspection parameters 1006 from one or more sensors 602 to discern the elastic strand from a wrinkle during production.

Combinations

A. A method for inspecting absorbent articles, the method comprising the steps of: preprocessing each image of a group of images of absorbent articles to label a component of the absorbent article; generating a first inspection algorithm with a convolutional neural network based on the preprocessed images, wherein the first inspection algorithm is usable to mask the labeled component in images of absorbent articles; providing a second inspection algorithm, wherein the second inspection algorithm is usable to determine one or more properties of the labeled component in images of absorbent articles, wherein the one or more properties comprise any of a location, a size, a shape, and a presence of the component; providing a communication network; connecting a sensor with the communication network; connecting a controller with the communication network, the controller comprising the first inspection algorithm; advancing a substrate through a converting process; sequentially adding component parts to the substrate; creating images of at least one of the substrate and component parts with the sensor; communicating the images from the sensor to the controller; masking the labeled component in the images by analyzing the images with the first inspection algorithm; determining at least one of the properties for the labeled component in the substrate with the second inspection algorithm; cutting the substrate with component parts added thereto into discrete absorbent articles; and based on the determination of the least one of the properties for the labeled component in the substrate, executing a control action, wherein the control action is any of rejecting one or more of the discrete absorbent articles, an automatic phase adjustment, an automatic tracking adjustment, a machine maintenance scheduling, and a machine stop command.

B. The method according to paragraph A, wherein the controller comprises any of a field programmable gate array, a graphics processing unit, and a central processing unit.

C. The method according to paragraphs A-B, wherein the component parts include parts added as a continuous web of material and parts added as a discontinuous web of material.

D. The method according to paragraphs A-C, wherein the communication network comprises any of an Ethernet protocol, a USB protocol, a FireWire protocol, and a CameraLink protocol.

E. The method according to paragraphs A-D, wherein the labeled component comprises any of a contaminant and an undesirable transformation of the absorbent article.

F. The method according to paragraph E, wherein the undesirable transformation of the absorbent article comprises any of a hole, a tear, and a wrinkle.

G. The method according to paragraphs A-F, wherein determining the at least one of the properties for the labeled component in the substrate with the second inspection algorithm comprises determining an angular orientation of the labeled component.

H. The method according to paragraphs A-G, wherein determining the at least one of the properties for the labeled component in the substrate with the second inspection algorithm comprises determining the absence of the labeled component.

I. The method according to paragraphs A-H, wherein determining the at least one of the properties for the labeled component in the substrate with the second inspection algorithm comprises determining a texture of the labeled component.

J. The method according to paragraphs A-I, wherein determining the at least one of the properties for the labeled component in the substrate with the second inspection algorithm comprises determining a total number of the labeled components.

K. The method according to paragraphs A-J, wherein determining the at least one of the properties for the labeled component in the substrate with the second inspection algorithm comprises determining a deformation of the labeled component.

L. The method according to paragraphs A-K, wherein the absorbent articles are any of diapers and feminine hygiene products.

M. The method according to paragraph L, wherein the component parts comprise any of ears, tapes, graphics, elastics, core, cuts, and/or wrappers.

N. A method for inspecting absorbent articles, the method comprising the steps of: preprocessing each image of a group of images of absorbent articles to label a component of the absorbent article;—generating a first inspection algorithm with a convolutional neural network based on the preprocessed images, wherein the first inspection algorithm is usable to mask the labeled component in images of absorbent articles; providing a second inspection algorithm, wherein the second inspection algorithm is usable to determine one or more properties of the labeled component in images of absorbent articles, wherein the one or more properties comprise any of a location, a size, a shape, and a presence of the component; advancing a substrate through a converting process; sequentially adding component parts to the substrate; creating images of a substrate and one or more component parts; masking the labeled component in the images by analyzing the images with the first inspection algorithm; and determining at least one of the properties for the labeled component in the substrate with the second inspection algorithm.

O. The method according to paragraph N, further comprising cutting the substrate with component parts added thereto into discrete absorbent articles; and based on the determination of the least one of the properties for the labeled component in the substrate, executing a control action.

P. The method according to paragraph O, wherein the control action is any of rejecting one or more of the discrete absorbent articles, an automatic phase adjustment, an automatic tracking adjustment, a machine maintenance scheduling, and a machine stop command.

Q. The method according to paragraphs N-P, wherein determining the at least one of the properties for the labeled component in the substrate with the second inspection algorithm comprises any of determining an angular orientation of the labeled component, determining the absence of the labeled component, determining a texture of the labeled component, determining a total number of the labeled components, determining the presence of a contaminant, and determining an undesirable transformation of the labeled component.

R. A method for inspecting absorbent articles, the method comprising the steps of: storing a group of digitized signals of absorbent articles, wherein the digitized signals are preprocessed to label a component of the absorbent article; providing the preprocessed digitized signals to a training algorithm to create a convolutional neural network; generating a first inspection algorithm with the convolutional neural network based on the group of preprocessed digitized signals, wherein the first inspection algorithm masks one or more properties of the labeled component; providing a second inspection algorithm, wherein the second inspection algorithm is usable to determine one or more properties of the labeled component in digitized signals of absorbent articles, wherein the one or more properties comprise any of a location, a size, a shape, and a presence of the component; advancing a substrate through a converting process; sequentially adding component parts to the substrate; creating inspection data of at least one of the substrate and component parts with a sensor; communicating the inspection data from the sensor to a controller, wherein the controller comprises the first inspection algorithm; identifying the labeled component in the substrate by analyzing the inspection data with the first inspection algorithm; determining at least one of the properties for the labeled component in the substrate with the second inspection algorithm; and cutting the substrate with component parts added thereto into discrete absorbent articles.

S. The method according to paragraph R, further comprising the step of executing a control action based on the determination of the least one of the properties for the labeled component in the substrate, wherein the control action is selected from the group consisting of: adjusting an advancement speed of the substrate; adjusting a placement of component parts; and rejecting absorbent articles.

T. The method according to paragraphs R-S, wherein the digitized signals are selected from the group consisting of: images; profile signals; 3-D point cloud; height maps; and sensor data.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for inspecting absorbent articles, the method comprising steps of:

preprocessing each image of a group of images of absorbent articles to label a component of the absorbent article;

generating a first inspection algorithm with a convolutional neural network based on the preprocessed images, wherein the first inspection algorithm is usable to mask the labeled component in images of absorbent articles;

providing a second inspection algorithm, wherein the second inspection algorithm is usable to determine one or more properties of the labeled component in images of absorbent articles, wherein the one or more properties comprise any of a location, a size, a shape, and a presence of the component;

providing a sensor;

providing a controller, the controller comprising the first inspection algorithm;

advancing a substrate through a converting process;

creating images of the substrate with the sensor;

communicating the images from the sensor to the controller;

masking the labeled component in the images by analyzing the images with the first inspection algorithm;

determining at least one of the properties for the labeled component with the second inspection algorithm;

cutting the substrate into discrete absorbent articles; and based on the determination of the least one of the properties for the labeled component, executing a control action, wherein the control action is any of rejecting one or more of the discrete absorbent articles, an automatic phase adjustment, an automatic tracking adjustment, a machine maintenance scheduling, and a machine stop command.

2. The method of claim 1, wherein the controller comprises any of a field programmable gate array, a graphics processing unit, and a central processing unit.

3. The method of claim 1, wherein the labeled component comprises any of a contaminant and an undesirable transformation of the absorbent article.

4. The method of claim 3, wherein the undesirable transformation of the absorbent article comprises any of a hole, a tear, and a wrinkle.

5. The method of claim 1, wherein determining the at least one of the properties for the labeled component with the second inspection algorithm comprises determining an angular orientation of the labeled component.

6. The method of claim 1, wherein determining the at least one of the properties for the labeled component with the second inspection algorithm comprises determining the absence of the labeled component.

7. The method of claim 1, wherein determining the at least one of the properties for the labeled component with the second inspection algorithm comprises determining a texture of the labeled component.

8. The method of claim 1, wherein determining the at least one of the properties for the labeled component with the second inspection algorithm comprises determining a total number of the labeled components.

9. The method of claim 1, wherein determining the at least one of the properties for the labeled component with the second inspection algorithm comprises determining a deformation of the labeled component.

10. The method of claim 1, wherein the absorbent articles are any of diapers and feminine hygiene products.

11. The method of claim 1, further comprising a step of storing process data or product data.

12. A method for inspecting absorbent articles, the method comprising steps of:

preprocessing each image of a group of images of absorbent articles to label a component of the absorbent article;

generating a first inspection algorithm with a convolutional neural network based on the preprocessed images, wherein the first inspection algorithm is usable to mask the labeled component in images of absorbent articles;

providing a second inspection algorithm, wherein the second inspection algorithm is usable to determine one or more properties of the labeled component in images of absorbent articles, wherein the one or more properties comprise any of a location, a size, a shape, and a presence of the component;

advancing a substrate through a converting process;

creating images of the substrate;

masking the labeled component in the images by analyzing the images with the first inspection algorithm; and determining at least one of the properties for the labeled component with the second inspection algorithm.

13. The method of claim 12, further comprising:

cutting the substrate into discrete absorbent articles; and based on the determination of the least one of the properties for the labeled component, executing a control action.

14. The method of claim 13, wherein the control action is any of rejecting one or more of the discrete absorbent articles, an automatic phase adjustment, an automatic tracking adjustment, a machine maintenance scheduling, and a machine stop command.

15. The method of claim 14, wherein determining the at least one of the properties for the labeled component with the second inspection algorithm comprises any of determining an angular orientation of the labeled component, determining the absence of the labeled component, determining a texture of the labeled component, determining a total number of the labeled components, determining the presence of a contaminant, and determining an undesirable transformation of the labeled component.

16. The method of claim 12, further comprising a step of storing process data or product data.

17. A method for inspecting absorbent articles, the method comprising steps of:

storing a group of digitized signals of absorbent articles, wherein the digitized signals are preprocessed to label a component of the absorbent article;

providing the preprocessed digitized signals to a training algorithm to create a convolutional neural network;

generating a first inspection algorithm with the convolutional neural network based on the group of preprocessed digitized signals, wherein the first inspection algorithm masks one or more properties of the labeled component;

providing a second inspection algorithm, wherein the second inspection algorithm is usable to determine one or more properties of the labeled component in digitized signals of absorbent articles, wherein the one or more properties comprise any of a location, a size, a shape, and a presence of the component;

advancing a substrate through a converting process;

creating inspection data of the substrate with a sensor;

communicating the inspection data from the sensor to a controller, wherein the controller comprises the first inspection algorithm;

identifying the labeled component by analyzing the inspection data with the first inspection algorithm;

determining at least one of the properties for the labeled component with the second inspection algorithm; and cutting the substrate into discrete absorbent articles.

18. The method of claim 17, further comprising the step of executing a control action based on the determination of the least one of the properties for the labeled component, wherein the control action is selected from the group consisting of: adjusting an advancement speed of the substrate; adjusting a placement of component parts; and rejecting absorbent articles.

19. The method of claim 17, wherein the digitized signals are selected from the group consisting of: images; profile signals; 3-D point cloud; height maps; and sensor data.

20. The method of claim 17, further comprising a step of storing process data or product data.

* * * * *